(12) United States Patent
Barreiro et al.

(10) Patent No.: US 12,186,202 B2
(45) Date of Patent: *Jan. 7, 2025

(54) INTERBODY FUSION DEVICE COMPRISING TEXTURED SURFACES

(71) Applicant: SPINE WAVE, INC., Shelton, CT (US)

(72) Inventors: Peter Barreiro, Trumbull, CT (US); Scott McLean, Sandy Hook, CT (US); Daniel Vigliotti, Guilford, CT (US)

(73) Assignee: SPINE WAVE, INC., Shelton, CT (US)

( * ) Notice: Subject to any disclaimer, the term of this patent is extended or adjusted under 35 U.S.C. 154(b) by 177 days.

This patent is subject to a terminal disclaimer.

(21) Appl. No.: 17/892,076

(22) Filed: Aug. 20, 2022

(65) Prior Publication Data

US 2022/0387183 A1 Dec. 8, 2022

Related U.S. Application Data

(62) Division of application No. 17/547,640, filed on Dec. 10, 2021, now Pat. No. 11,419,735.

(Continued)

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4601* (2013.01); *A61F 2/4611* (2013.01);
(Continued)

(58) Field of Classification Search
CPC .......... A61F 2/44; A61F 2/4455; A61F 2/446; A61F 2/4465; A61F 2/447; A61F 2/4611
See application file for complete search history.

(56) References Cited

U.S. PATENT DOCUMENTS

| 4,330,891 A | 5/1982 | Branemark et al. |
| 4,451,254 A | 5/1984 | Dinius et al. |

(Continued)

FOREIGN PATENT DOCUMENTS

| CN | 202458786 U | 10/2012 |
| EP | 2386274 A1 | 11/2011 |

(Continued)

OTHER PUBLICATIONS

Martinez-Calderon et al., "Surface micro- and nano-texturing of stainless steel by femtosecond laser for the control of cell migration", Scientific Reports, vol. 6, 10 pages, Nov. 2, 2016.

(Continued)

*Primary Examiner* — Eric S Gibson
(74) *Attorney, Agent, or Firm* — Hoffmann & Baron, LLP

(57) ABSTRACT

An expandable interbody fusion device and an associated instrument for inserting the device into an intervertebral disc space, expanding the device and for use in delivering graft material into the device once expanded in the disc space. The device is small enough to fit through Kambin's triangle yet is capable of expanding both in the vertical direction to accommodate spinal lordosis and in the lateral direction to provide sufficient structural support for opposing vertebral bodies laterally within the disc space. A process of forming textured top and bottom surfaces of the device by initially laser ablating each surface with a nano-second pulsed laser followed by laser ablating those surfaces with a femtosecond pulsed laser.

17 Claims, 16 Drawing Sheets

Related U.S. Application Data

(60) Provisional application No. 63/127,316, filed on Dec. 18, 2020.

(51) Int. Cl.
*A61F 2/28* (2006.01)
*A61F 2/30* (2006.01)

(52) U.S. Cl.
CPC .............. *A61F 2002/2835* (2013.01); *A61F 2002/30123* (2013.01); *A61F 2002/30261* (2013.01); *A61F 2002/30354* (2013.01); *A61F 2002/30494* (2013.01); *A61F 2002/30556* (2013.01); *A61F 2002/30579* (2013.01); *A61F 2002/30593* (2013.01); *A61F 2002/30772* (2013.01); *A61F 2002/3097* (2013.01); *A61F 2310/00023* (2013.01)

(56) References Cited

U.S. PATENT DOCUMENTS

| | | | |
|---|---|---|---|
| 4,553,272 A | 11/1985 | Mears | |
| 5,246,530 A | 9/1993 | Bugle et al. | |
| 5,473,138 A | 12/1995 | Singh et al. | |
| 5,603,338 A | 2/1997 | Beaty | |
| 5,716,412 A | 2/1998 | DeCarlo et al. | |
| 5,965,006 A | 10/1999 | Baege et al. | |
| 6,129,763 A * | 10/2000 | Chauvin | A61F 2/4455 623/17.11 |
| 6,419,491 B1 | 7/2002 | Ricci et al. | |
| 6,443,989 B1 * | 9/2002 | Jackson | A61F 2/447 606/247 |
| 6,562,074 B2 | 5/2003 | Gerbec et al. | |
| 6,767,366 B2 | 7/2004 | Lee et al. | |
| 6,951,627 B2 * | 10/2005 | Li | B23K 26/04 219/121.75 |
| 6,955,691 B2 * | 10/2005 | Chae | A61F 2/447 623/17.11 |
| 6,979,346 B1 | 12/2005 | Hossainy et al. | |
| 7,018,418 B2 | 3/2006 | Amrich et al. | |
| 7,217,293 B2 * | 5/2007 | Branch, Jr. | A61F 2/4611 623/17.11 |
| 7,655,046 B2 * | 2/2010 | Dryer | A61F 2/446 623/17.11 |
| 7,682,937 B2 | 3/2010 | Evertsen et al. | |
| 7,850,862 B2 | 12/2010 | Amrich et al. | |
| 7,879,098 B1 * | 2/2011 | Simmons, Jr. | A61F 2/4465 623/17.11 |
| 8,187,255 B2 | 5/2012 | Weber et al. | |
| 8,221,502 B2 * | 7/2012 | Branch, Jr. | A61F 2/447 623/17.11 |
| 8,323,349 B2 | 12/2012 | Schmid | |
| 8,394,129 B2 | 3/2013 | Morganstern-Lopez et al. | |
| 8,414,654 B1 | 4/2013 | Ganey | |
| 8,715,351 B1 | 5/2014 | Pinto | |
| 8,764,444 B2 | 7/2014 | Hansson | |
| 9,125,756 B2 | 9/2015 | Ulrich et al. | |
| 9,295,562 B2 * | 3/2016 | Lechmann | A61F 2/44 |
| 9,339,395 B2 | 5/2016 | Prado et al. | |
| 9,408,717 B2 | 8/2016 | Perrow | |
| 9,452,484 B2 | 9/2016 | Oliver Vargas | |
| 9,844,444 B2 | 12/2017 | Wolfe et al. | |
| 9,925,295 B2 | 3/2018 | McEntire et al. | |
| 10,039,650 B2 * | 8/2018 | Lamborne | A61F 2/447 |
| 10,111,753 B2 | 10/2018 | Patterson | |
| 10,358,723 B2 | 7/2019 | Vaidyanathan et al. | |
| 10,478,311 B2 | 11/2019 | Miccio et al. | |
| 10,492,924 B2 | 12/2019 | Stein et al. | |
| 10,492,925 B2 | 12/2019 | Hollister et al. | |
| 10,555,820 B2 * | 2/2020 | Tseng | A61B 17/8858 |
| 10,603,093 B2 * | 3/2020 | Lin | A61B 17/866 |
| 10,993,816 B2 * | 5/2021 | Kieser | A61B 90/90 |
| 11,166,824 B2 | 11/2021 | Miccio et al. | |
| 11,219,531 B2 * | 1/2022 | Lemoine | A61F 2/446 |
| 11,253,369 B2 * | 2/2022 | Tseng | A61B 17/8816 |
| 11,419,735 B2 * | 8/2022 | Barreiro | A61F 2/4601 |
| 2002/0040243 A1 | 4/2002 | Attali et al. | |
| 2002/0143401 A1 * | 10/2002 | Michelson | A61F 2/446 606/264 |
| 2005/0021041 A1 * | 1/2005 | Michelson | A61F 2/446 606/249 |
| 2005/0113916 A1 * | 5/2005 | Branch, Jr. | A61F 2/447 623/17.11 |
| 2005/0113917 A1 * | 5/2005 | Chae | A61F 2/447 623/17.11 |
| 2006/0000814 A1 | 1/2006 | Gu et al. | |
| 2009/0082810 A1 | 3/2009 | Bhatnagar et al. | |
| 2010/0234956 A1 * | 9/2010 | Attia | A61F 2/447 606/279 |
| 2011/0106261 A1 | 5/2011 | Chin et al. | |
| 2011/0112587 A1 | 5/2011 | Patel et al. | |
| 2012/0226357 A1 * | 9/2012 | Varela | A61F 2/447 623/17.16 |
| 2012/0312778 A1 * | 12/2012 | Ullrich, Jr. | C23C 14/34 451/28 |
| 2012/0316650 A1 | 12/2012 | Ullrich et al. | |
| 2013/0110243 A1 | 5/2013 | Patterson et al. | |
| 2013/0123925 A1 | 5/2013 | Patterson et al. | |
| 2013/0282122 A1 * | 10/2013 | Ullrich, Jr. | A61F 2/4465 623/17.16 |
| 2014/0039622 A1 * | 2/2014 | Glerum | A61F 2/447 623/17.15 |
| 2014/0067071 A1 * | 3/2014 | Weiman | A61F 2/4611 623/17.16 |
| 2014/0257486 A1 * | 9/2014 | Alheidt | A61F 2/4455 623/17.15 |
| 2015/0018958 A1 * | 1/2015 | Ullrich, Jr. | A61F 2/3094 29/557 |
| 2016/0183990 A1 * | 6/2016 | Koizumi | A61B 17/8085 606/285 |
| 2017/0151004 A1 * | 6/2017 | Lin | A61B 17/846 |
| 2017/0258600 A1 * | 9/2017 | Tseng | A61B 17/8852 |
| 2018/0193164 A1 * | 7/2018 | Shoshtaev | A61F 2/4455 |
| 2018/0296343 A1 | 10/2018 | Wei | |
| 2018/0360615 A1 | 12/2018 | Miller et al. | |
| 2019/0076266 A1 | 3/2019 | Trudeau et al. | |
| 2019/0133784 A1 * | 5/2019 | Gunn | A61F 2/4455 |
| 2019/0328406 A1 * | 10/2019 | Lu | A61B 17/1671 |
| 2020/0171202 A1 * | 6/2020 | Spence | A61B 17/7291 |
| 2020/0323641 A1 * | 10/2020 | Lemoine | A61F 2/4455 |
| 2020/0345465 A1 * | 11/2020 | Ishiwata | A61C 8/0022 |
| 2020/0352731 A1 * | 11/2020 | Berry | A61F 2/447 |
| 2020/0352738 A1 * | 11/2020 | Berry | A61F 2/4455 |
| 2021/0137695 A1 * | 5/2021 | Huang | A61F 2/4455 |
| 2021/0186706 A1 * | 6/2021 | Spitler | A61F 2/44 |
| 2022/0192840 A1 * | 6/2022 | Barreiro | A61F 2/4601 |

FOREIGN PATENT DOCUMENTS

| | | | | |
|---|---|---|---|---|
| EP | 3818964 A1 * | 5/2021 | | A61F 2/4455 |
| KR | 10-2020-0060906 A | 6/2020 | | |
| KR | 10-2020-0106613 A | 9/2020 | | |
| WO | 2005051244 A1 | 6/2005 | | |
| WO | 2009046517 A1 | 4/2009 | | |
| WO | 2013142480 A1 | 9/2013 | | |
| WO | 2014018325 A1 | 1/2014 | | |
| WO | WO-2014164625 A1 * | 10/2014 | | A61F 2/442 |
| WO | 2015/030228 A1 | 5/2015 | | |
| WO | 2016130878 A1 | 8/2016 | | |
| WO | WO-2018183464 A1 * | 10/2018 | | A01N 25/10 |
| WO | WO-2021072237 A1 * | 4/2021 | | A61F 2/4455 |

OTHER PUBLICATIONS

International Search Report for PCT/US2021/062822, mailed May 30, 2022.
Written Opinion for PCT/US2021/062822, mailed May 30, 2022.
M. Hardenbrook et al., "The Anatomic Rationale for Transforaminal Endoscopic Interbody Fusion: a Cadaveric Analysis", Neurosurgical Focus, vol. 40, Feb. 2016.

(56) References Cited

OTHER PUBLICATIONS

Dumas et al., "Femtosecond laser nano/micro patterning of titanium influences mesenchymal stem cell adhesion and commitment", Biomedical Materials, vol. 10, No. 5, Sep. 3, 2015.
Dumas et al., "Multiscale grooved titanium processed with femtosecond laser influences mesenchymal stem cell morphology, adhesion, and matrix organization", Journal of Biomedical Materials Research, Part A, vol. 100a (11):3108-3116, Jul. 13, 2012.

* cited by examiner

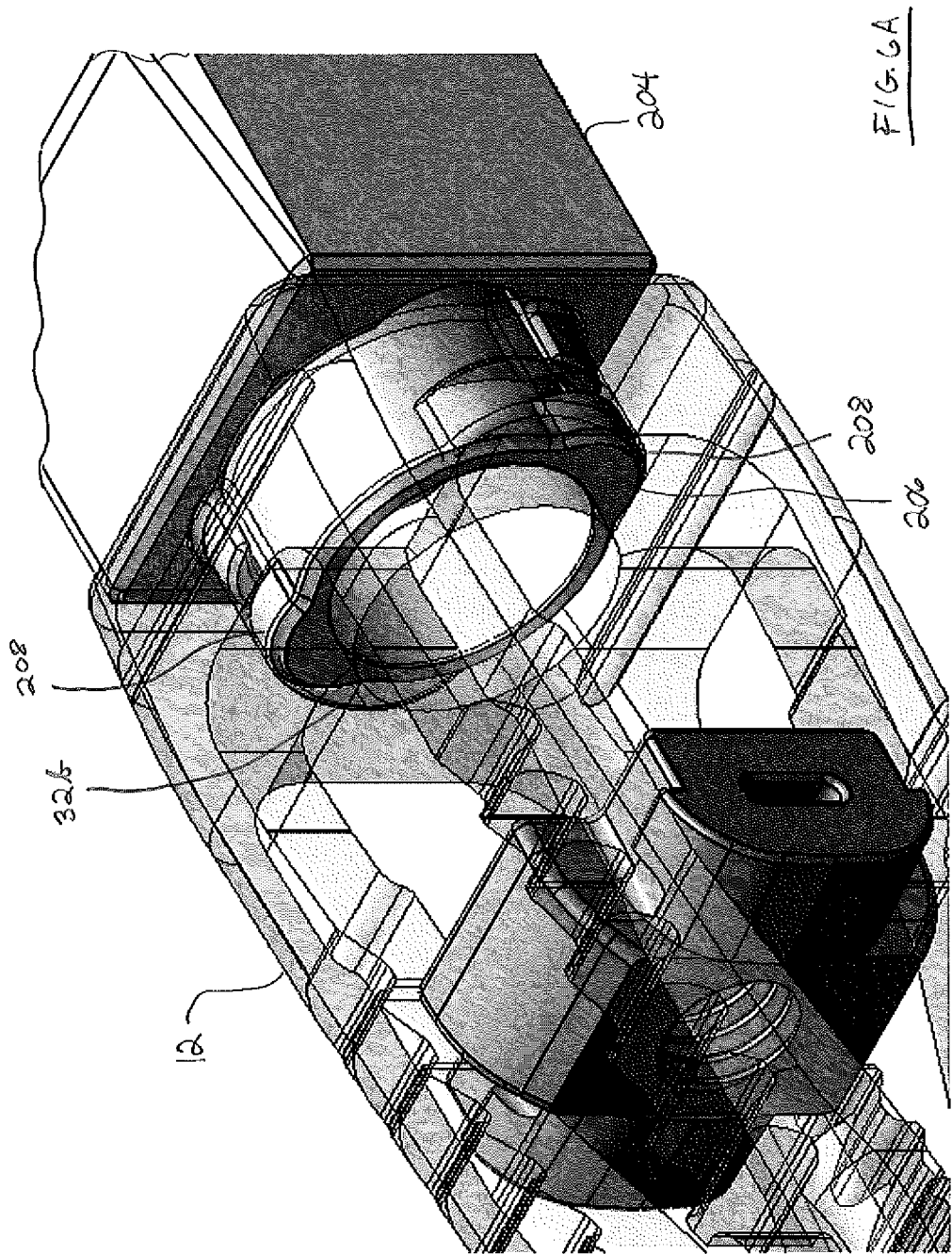

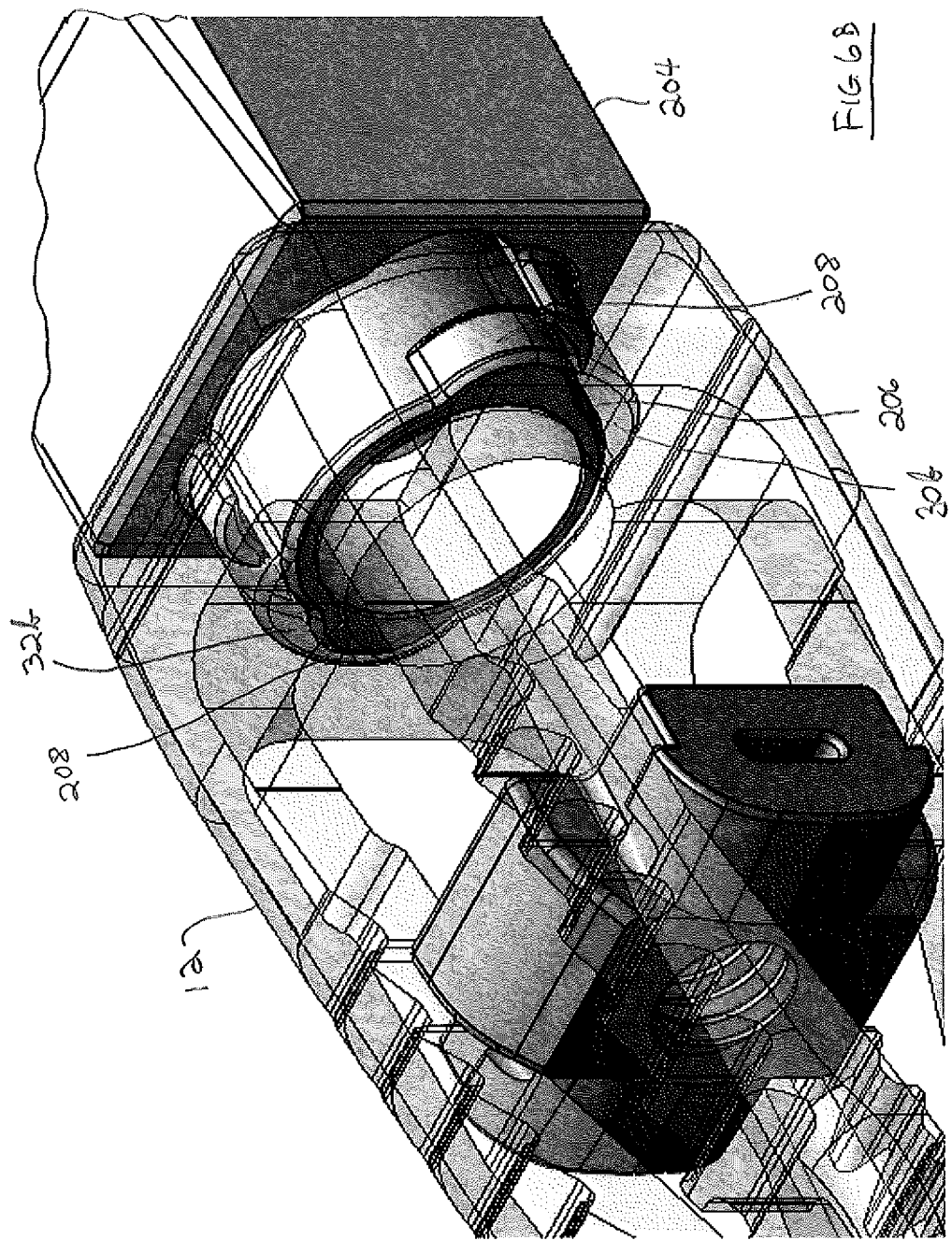

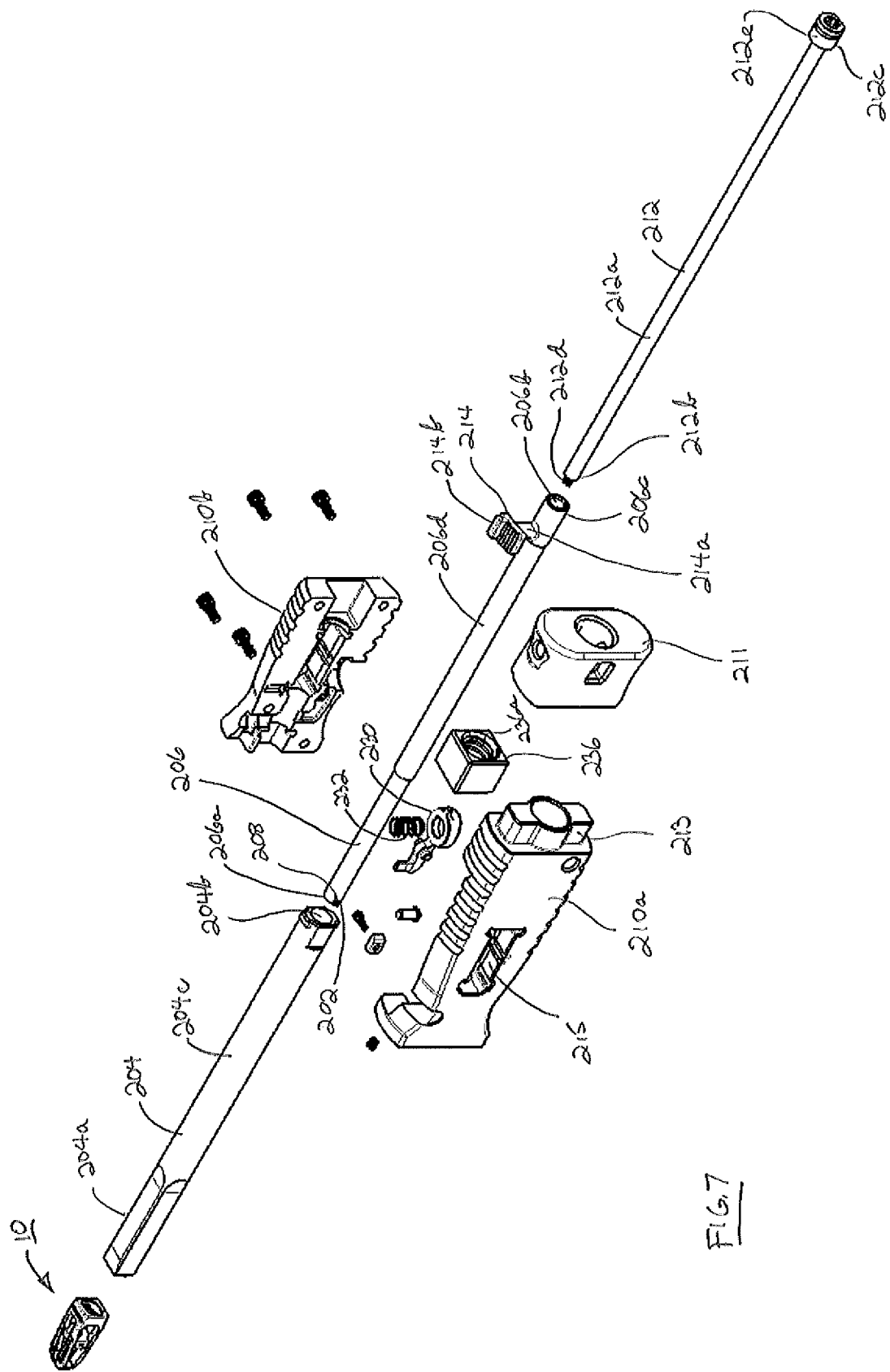

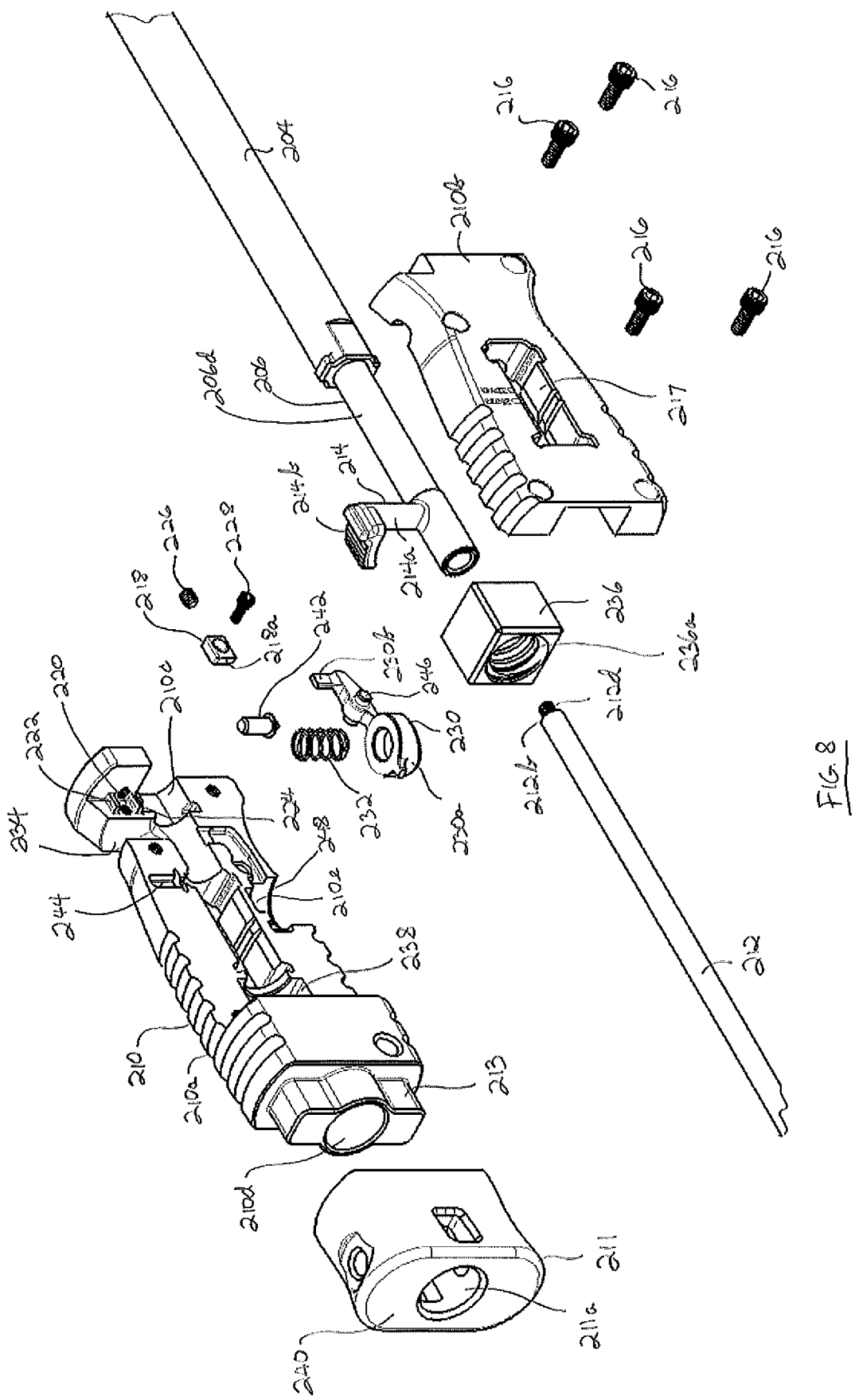

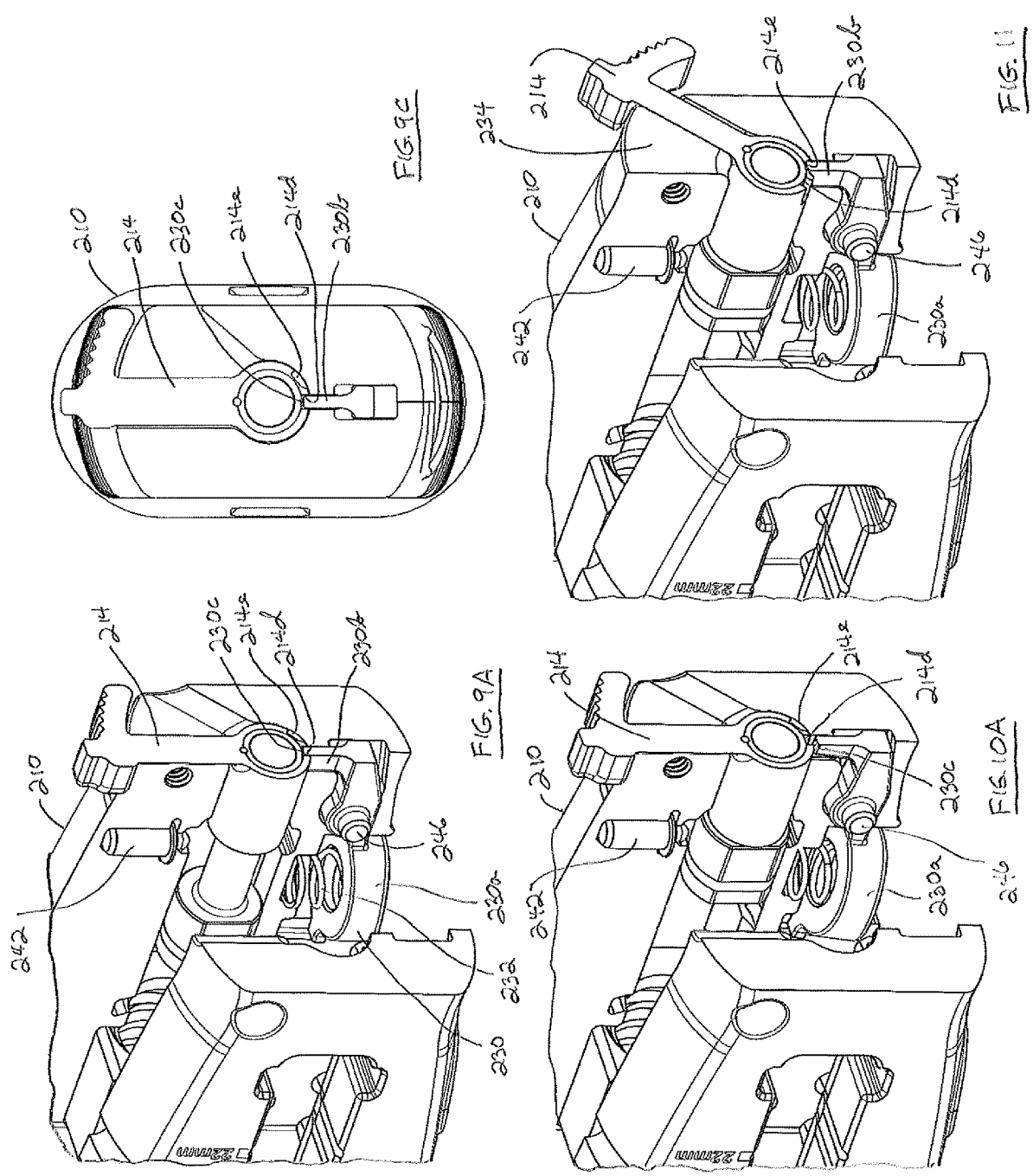

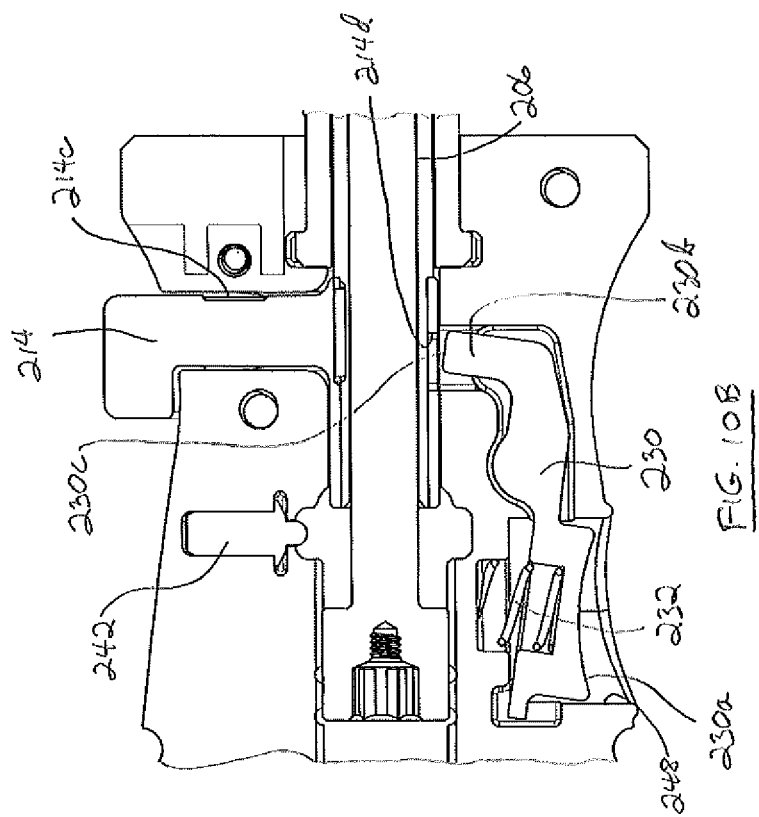
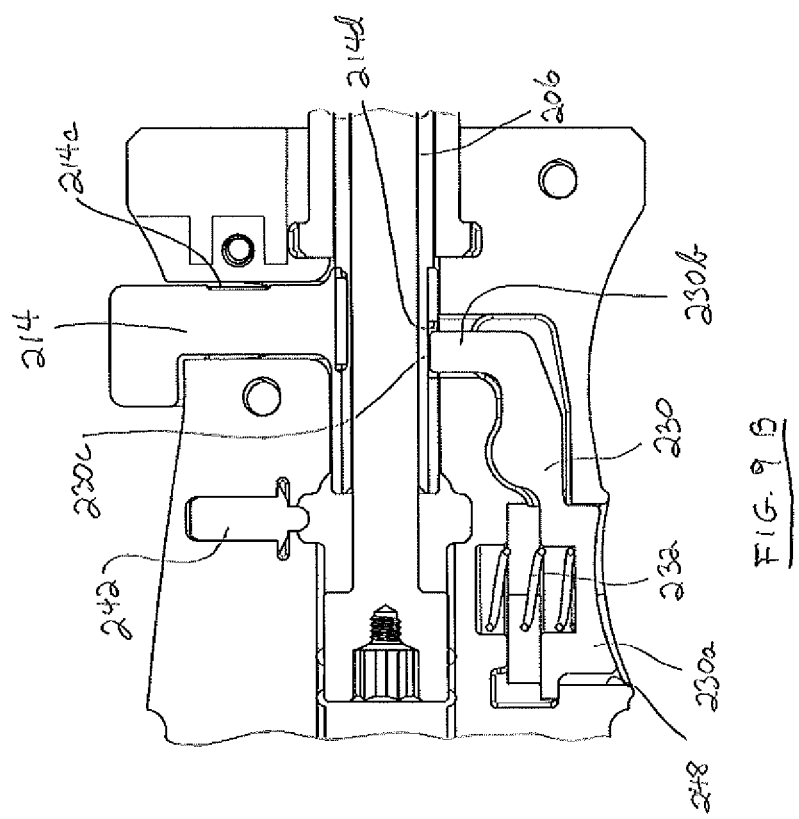

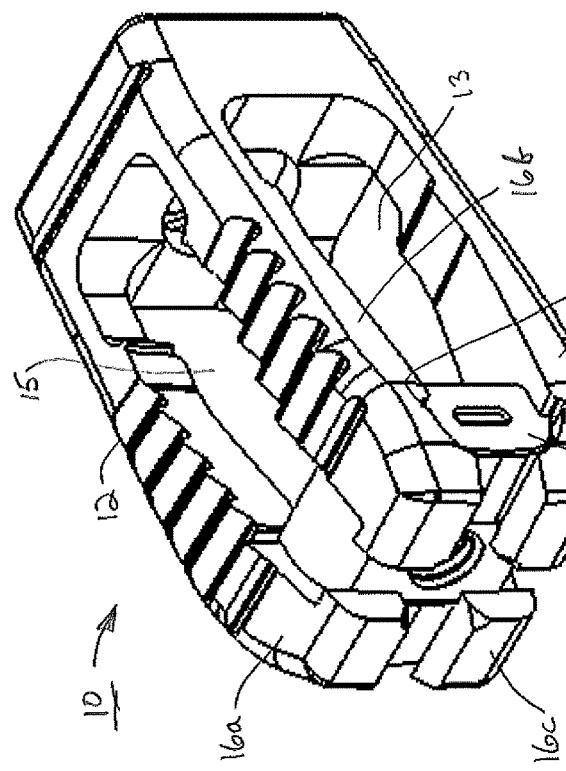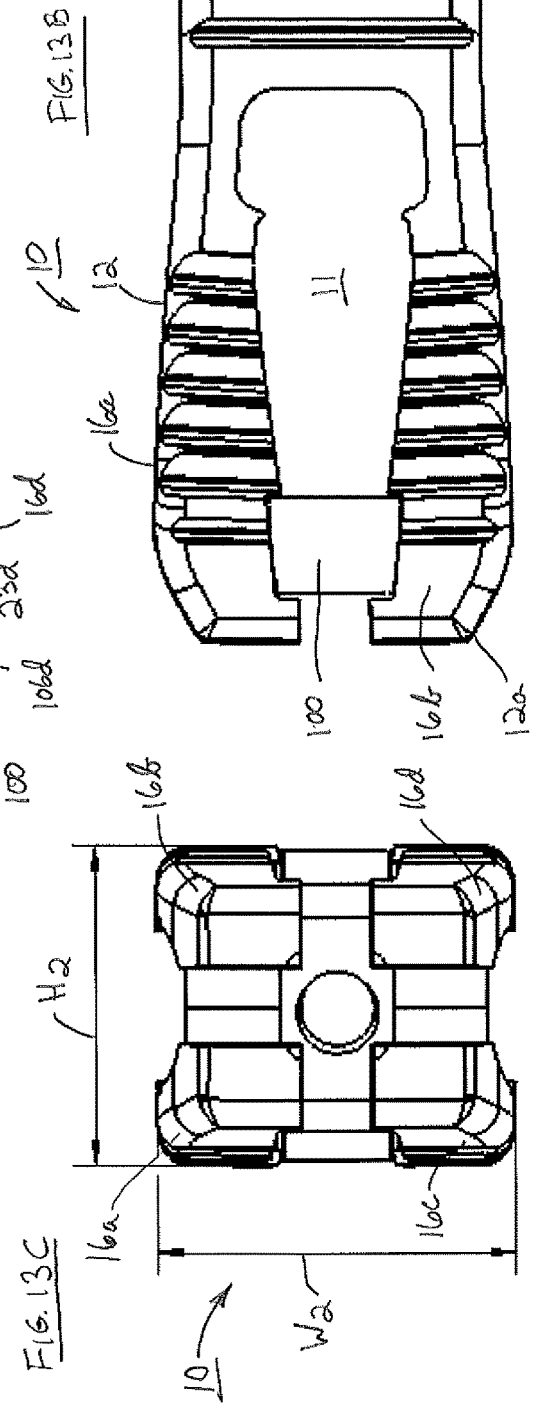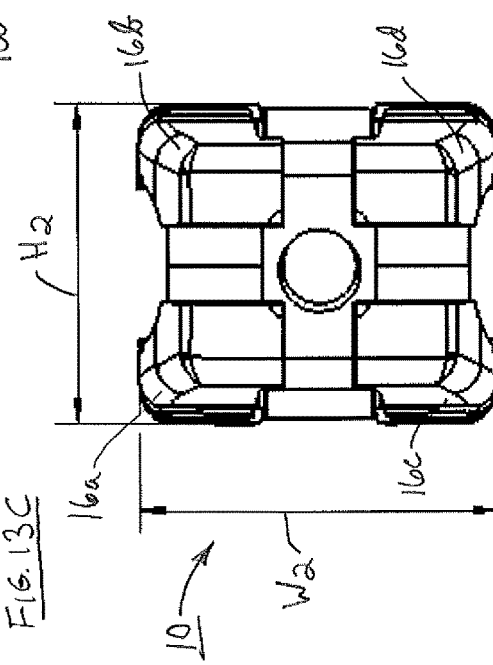

INTERBODY FUSION DEVICE COMPRISING TEXTURED SURFACES

CROSS-REFERENCE TO RELATED APPLICATION

This application is a divisional application of U.S. application Ser. No. 17/547,640, filed Dec. 10, 2021, now U.S. Pat. No. 11,419,735, which claims the benefit of U.S. Provisional Patent Application No. 63/127,316, filed Dec. 18, 2020, the entire contents of which are incorporated by reference herein.

FIELD OF THE INVENTION

The subject invention relates generally to the field of spinal implants and more particularly to an expandable transforaminal interbody fusion (TLIF) device and associated instrumentation for inserting the TLIF device into the disc space of a patient and introducing grafting material therein after the device is expanded.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

There are a variety of implants for spinal fusion in current use, some of which are expandable and others of fixed dimension. In order to accommodate the spinal anatomy and promote arthrodesis, an interbody fusion device preferably has optimized contact with adjacent endplates. This is commonly achieved by ensuring that the interface between the device and the bony endplates of opposing vertebral bodies includes a surface area as large as practicable. Expandable interbody fusion devices have been particularly used for this purpose. With the advent of minimally invasive spinal surgery, additional efforts have been introduced to further decrease the trauma to the patient during spinal surgery. In this manner, expandable interbody fusion devices have been sized and configured in a smaller size to be used in a posterolateral approach through what is known as Kambin's triangle. Smaller sized interbody fusion devices typically result in, among other things, a smaller incision, decreased blood loss and shorter patient recovery. Examples of interbody fusion devices sized and configured to fit through Kambin's triangle during introduction into the interbody disc space are shown in U.S. Pat. No. 9,408,717, entitled "Expandable Intervertebral Device, and Systems and Methods for Inserting Same", issued on Apr. 9, 2016 to Scott J. Perrow, which describes an expandable interbody fusion device that expands to increase the height of the disc space, and U.S. Pat. No. 9,844,444, entitled "Far Lateral Spacer", issued on Dec. 19, 2017 to Steve Wolfe et al., which describes an expandable interbody fusion device that expands laterally within the disc space.

While expandable interbody fusion devices sized and configured to fit through Kambin's triangle have certain surgical benefits they raise other challenges relating to their insertion and the subsequent introduction of grafting material, particularly due to their relatively small size.

Accordingly, there is a need to develop an expandable interbody fusion device configured to be used in a transforaminal lumbar interbody fusion (TLIF) procedure that can be inserted into the interbody disc space through Kambin's triangle with suitable insertion and grafting instruments.

SUMMARY OF THE INVENTION

It is an object of the invention to provide an interbody fusion device with improved capability for attachment to an insertion instrument.

It is another object of the invention to provide an improved interbody fusion apparatus that includes an interbody fusion device and an instrument attachable to the device for inserting the interbody fusion device into an intravertebral disc space, It is a further object of the invention to provide an improved instrument for inserting an interbody fusion device into an intravertebral disc space and for delivering graft material thereto.

It is yet another object of the invention to provide a process of forming textured surfaces on top and bottom surfaces of an interbody fusion device.

DESCRIPTION OF THE FIGURES

FIGS. 6A and 6B are images of the process of attaching the instrument to the interbody fusion device.

FIG. 7 is an exploded top, front perspective view of the instrument of FIG. 1.

FIG. 8 is an enlarged exploded view of a portion of the instrument of FIG. 7.

FIG. 9A is an exploded perspective view of a sectioned portion of the instrument handle showing details of the locking structure for locking the instrument to the interbody fusion device with the locking button in a locked position.

FIG. 9B is a side sectional view of the portion of the instrument handle depicted in FIG. 9A.

FIG. 9C is a longitudinal sectional view of the portion of the instrument handle depicted in FIG. 9A FIG. 10A is a further view of FIG. 9A showing the locking button in an unlocked position.

FIG. 10B is a further view of FIG. 9B showing the locking button in an unlocked position.

FIG. 11 is a further view similar to FIG. 10A showing the locking handle moved to a position allowing the instrument to be separated from the interbody fusion device.

FIG. 13A is a top, front perspective view of the interbody fusion device of FIG. 1 in an expanded condition.

FIG. 13B is a top plan view of the expanded interbody fusion device of FIG. 10A.

FIG. 13C is a front elevation view of the expanded interbody fusion device of FIG. 13A.

DESCRIPTION OF THE EMBODIMENTS

Figure 1:
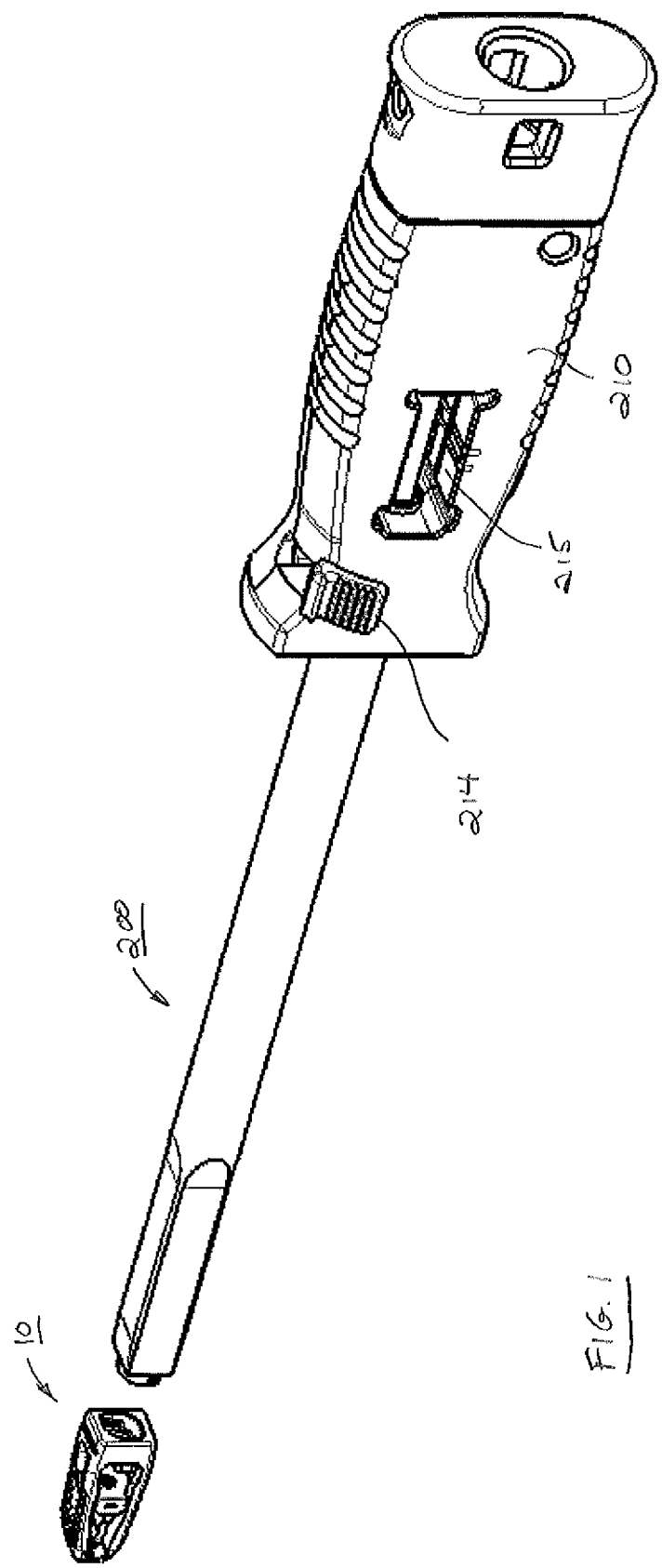
FIG. 1 is an exploded top, front perspective view of an expandable interbody fusion device and an associated instrument for attachment to and use with the device according to an embodiment of the present invention.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, there is shown an expandable interbody fusion device 10 and an associated instrument 200 for inserting device 10 into an intervertebral disc space, expanding device 10 and for use in delivering graft material into device 10 once expanded within the disc space. In accordance with a particular arrangement, device 10 and instrument 200 are sized and configured for introducing device 10 in a posterolateral approach through Kambin's triangle in a transforaminal lumbar interbody fusion (TLIF) procedure. Kambin's triangle is well known and is defined as a right triangle over the dorsolateral disc: the hypotenuse is the exiting nerve root, the base (width) is the superior border of the caudal vertebra, and the height is the traversing nerve root, (See M. Hardenbrook et al., "The Anatomic Rationale for the Transforaminal Endoscopic Interbody Fusion: a Cadaveric Analysis", Neurosurgical Focus Volume 40, February 2016, incorporated herein by reference). As will be described, device 10 is small enough to fit through Kambin's triangle yet is capable of expanding both in the vertical direction to accommodate spinal lordosis and in the lateral direction to provide sufficient structural support for opposing vertebral bodies laterally within the disc space. It should be appreciated that while device 10 is particularly configured for use as spinal implant in a TLIF procedure, it is not limited to use through Kambin;s triangle and, as such, may also be used as an expandable interbody fusion device that may be introduced in other approaches, such as in the posterior, anterior or lateral directions at different levels of the spine, or percutaneously.

Figure 2:
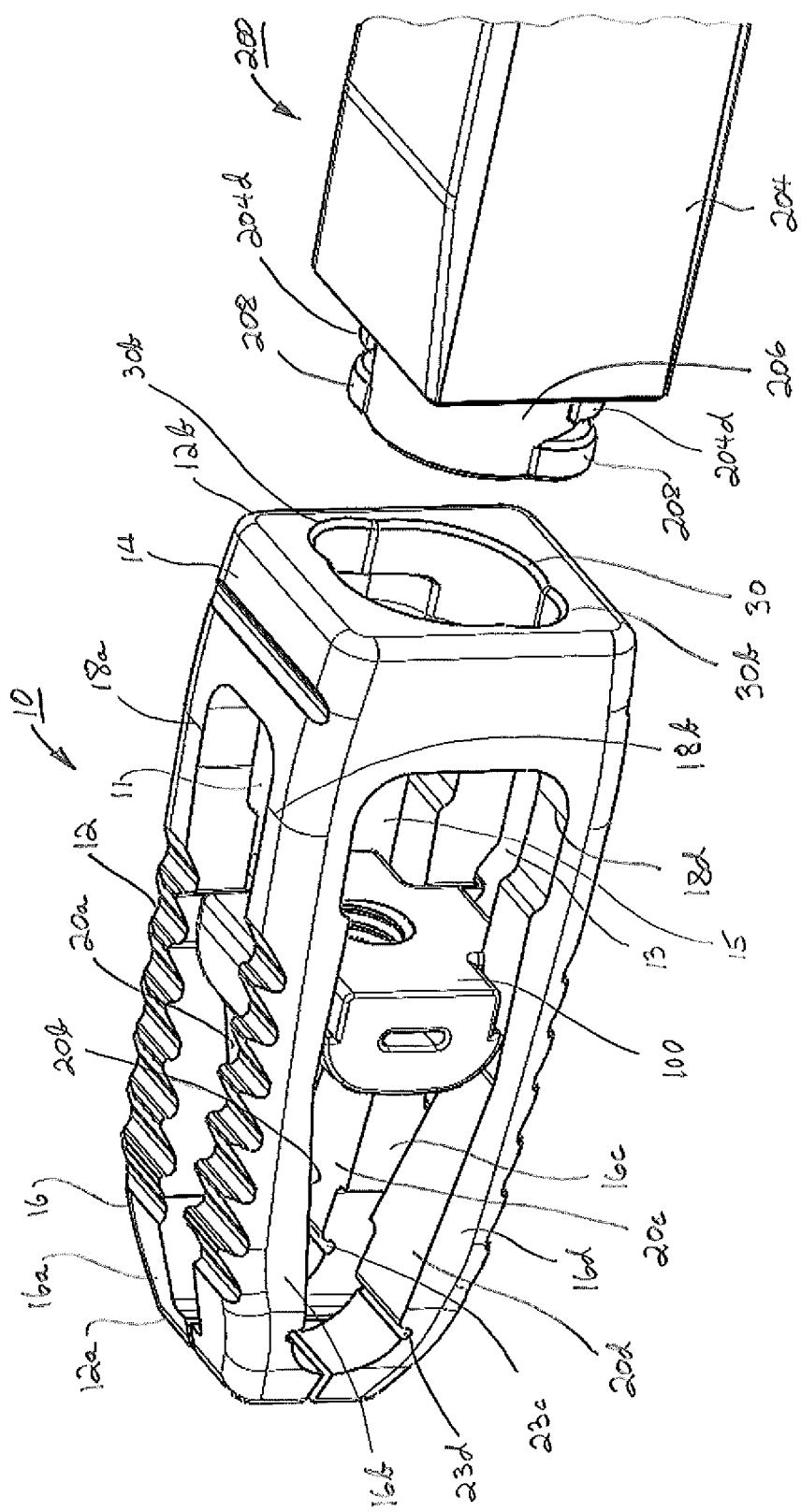
FIG. 2 is an enlarged view of FIG. 1 showing the expandable interbody fusion device and a portion of the distal end of the instrument.
Figure 3:
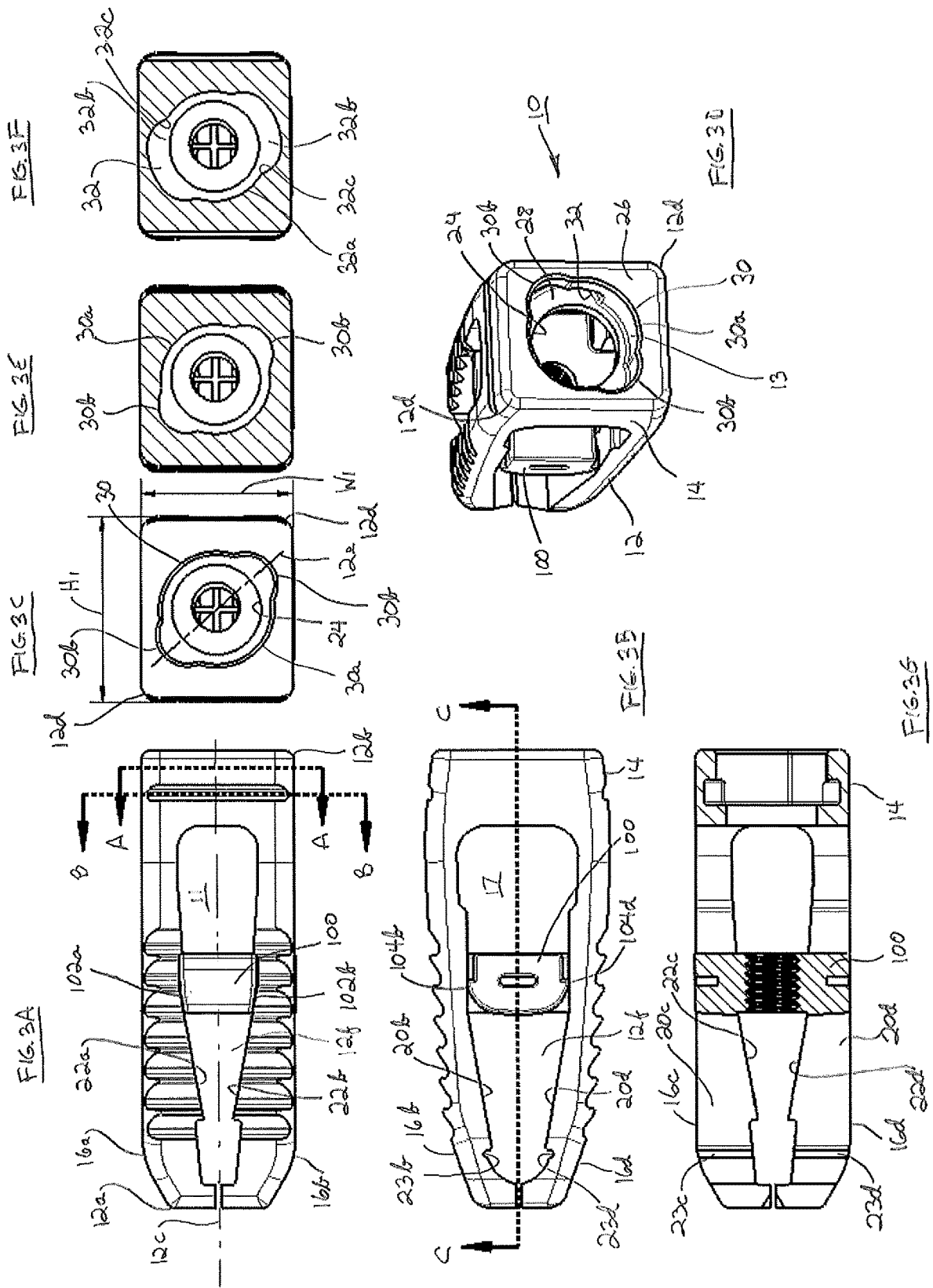
FIG. 3A is a top plan view of the interbody fusion device of FIG. 1.
FIG. 3B is a side elevation view of the interbody fusion device of FIG. 1.
FIG. 3C is a rear elevation view of the interbody fusion device of FIG. 1
FIG. 3D is a top, rear perspective view of the interbody fusion device of FIG. 1
FIG. 3E a cross-sectional view of the interbody fusion device as seen along viewing lines A-A of FIG. 3A.
FIG. 3F a cross-sectional view of the interbody fusion device as seen along viewing lines B-B of FIG. 3A.
FIG. 3G a cross-sectional view of the interbody fusion device as seen along viewing lines C-C of FIG. 3B.

Turning now to FIGS. 2 and 3A-3G details of expandable interbody fusion device 10 are described. Device 10 comprises a cage 12 having a hollow interior 12f and a wedge 100 slidable within said hollow interior 12f. Cage 12 has a distal end 12a and a proximal end 12b. Cage 12 is generally elongate defining a longitudinal axis 12c, as depicted in FIG. 3A, extending through distal end 12a and proximal end 12b. Wedge 100 is sized and configured to be slidably moved within cage 12 to expand cage 12, as will be described. Cage 12 includes a base 14 at the proximal end 12b and a plurality of flexibly movable arms 16 projecting from base 14 toward distal end 12a. Arms 16 are free and unattached to each other at distal end 12a thereby allowing cage 12 to expand at its distal end 12a. In the arrangement shown, cage 12 has four movable arms 16 including a pair of upper arms 16a and 16b and a pair of lower arms 16c and 16d. Arms 16 are attached respectively to base 14 at hinge points 18a, 18b, 18c (not seen) and 18d in a manner to allow deflection of arms 16 relative to base 14 in two transverse directions. Cage 12 further includes a top opening 11 between arms 16a and 16b, a bottom opening 13 between arms 16c and 16d, and a pair of side openings, one opening 15 between arms 16a and 16c and the other opening 17 between arms 16b and 16d (See also FIGS. 13A and 13B). In use, the transverse directions may be mutually orthogonal, namely in a vertical direction to expand the device height at distal end 12a and thereby accommodate lordosis in the disc space, and horizontally to increase the device width and hence the lateral support of opposing vertebral bodies within the disc space. FIG. 3C shows the unexpanded device height $H_1$ and the unexpanded device width $W_1$. In a particular arrangement, cage 10 may be formed monolithically as a unitary device to have a quadrangular shape, as shown in FIG. 3D. It should be understood that other cage shapes, such as cylindrical may also be used.

As seen in FIGS. 2 and 3G each of upper arm 16a and lower arm 16c includes an inclined cam surface 20a and 20c, respectively facing each other vertically, for cooperative engagement with wedge 100. Upper arm 16b and lower arm 16d also include similar inclined cam surfaces 20b and 20d as shown in FIGS. 2 and 3B that respectively face each other vertically for cooperative engagement with wedge 100. Each of upper arms 16a and 16b further includes an inclined cam surface 22a and 22b as shown in FIG. 3A, respectively facing each other laterally, for cooperative engagement with wedge 100. Each of lower arms 16c and 16d also include similar inclined cam surfaces 22c and 22d as shown in FIG. 3G that face each other laterally for cooperative engagement with wedge 100. Each of lower arms 16c and 16d additionally includes a locking notch 23c and 23d as shown in FIG. 3G, while each of upper arms 16a and 16b additionally includes a locking notch 23a (not seen) and 23b, shown in FIG. 3B. Locking notches 23a, 23b, 23c and 23d, are each disposed adjacent distal end 12a of cage 12 for receipt of portions of wedge 100 to lock the plurality of arms 16 in the expanded position of cage 12.

Figure 4:
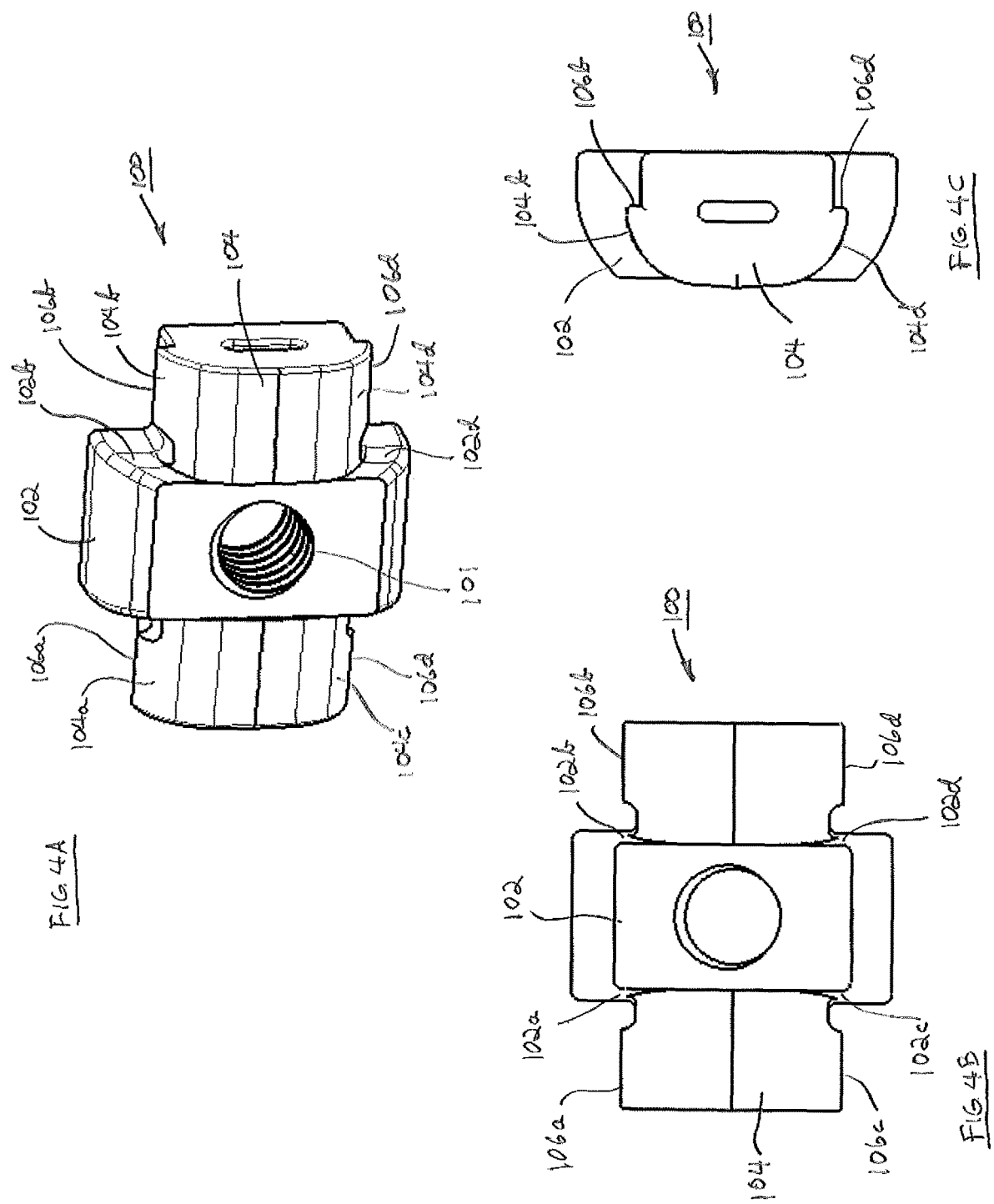
FIG. 4A is a top, front perspective view of the wedge for expanding the interbody fusion device of FIG. 1.
FIG. 4B is a front elevation view of the wedge of FIG. 4A.
FIG. 4C is a side elevation view of the wedge of FIG. 4A.

Referring now to FIGS. 4A-4C details of wedge 100 are described. Wedge 100 serves as an expander of device 10 and is sized and configured to be movably contained within cage 12 to expand the distal end 12a of cage 12 upon distal movement. Wedge 100 is generally cruciform in shape and has a threaded hole 101 extending generally centrally therethrough for threaded engagement with a threaded shaft of instrument 200, as will be described. Wedge 100 has a vertical section 102 and a transverse horizontal section 104 that in a particular arrangement lie mutually orthogonal to each other. Vertical section 102 has angled side surfaces 102a and 102b formed above horizontal section 104 and angled side surfaces 102c and 102d formed below horizontal section 104. During movement of wedge 100 in cage 12 toward distal end 12a, curved side surfaces 102a and 102b are arranged to respectively engage inclined cam surfaces 22a and 22b on upper arms 16a and 16b as shown in FIG. 3A, while angled side surfaces 102c and 102d are arranged to respectively engage inclined cam surfaces 22c and 22d on lower arms 16c and 16d. Such movement of wedge 100 and cooperative engagement with cage 12 will cause each of the distal ends of arms 16a, 16b, 16c and 16d to deflect laterally away from centerline 12c in a cantilevered manner about hinge points 18a, 18b, 18c and 18d to thereby expand the width of cage 12 at distal end 12a.

Horizontal section 104 has curved upper surfaces 104a and 104b formed on opposite lateral sides of vertical section 102 above horizontal section 104 and curved lower surfaces 104c and 104d formed on opposite lateral sides of vertical section 102 below horizontal section 104. As such, during movement of wedge 100 in cage 12 toward distal end 12a, curved upper surfaces 104b is arranged to engage inclined cam surface 20b on upper arms 16b while curved lower surface 104d is arranged to engage inclined cam surface 20d on lower arm 16d, as shown in FIG. 3B. Similarly, curved upper surfaces 104a is arranged to engage inclined cam surface 20a on upper arm 16a while curved lower surface 104c is arranged to engage inclined cam surface 20c on lower arm 16c. Such movement of wedge 100 and cooperative engagement with cage 12 will cause each of the distal ends of arms 16a, 16b, 16c and 16d to deflect vertically away from centerline 12c in a cantilevered manner about hinge points 18a, 18b, 18c and 18d to thereby expand the height of cage 12 at distal end 12a. In addition, each of curved upper surfaces 104a and 104b terminate respectively in an engagement edge 106a and 106b while each of curved lower surfaces 104c and 104d terminate respectively in an engagement edge 106c and 106d. Engagement edges are configured to engage and reside in respective locking notches 23a, 23b, 23c and 23d to lock cage 12 in the expanded position, as will be described.

In a particular arrangement, wedge 100 and inclined cam surfaces 20a-d and 22a-d on arms 16a-d are configured and oriented in manner to cause simultaneous movement of the plurality of arms 16. It should be appreciated that inclined surfaces 20a-d and 22a-d may also be configured and oriented relative to wedge 100 to cause sequential movement whereby the plurality of arms 16 are first moved in a lateral direction followed by movement in a vertical direction, or vice versa as desired.

Cage 12 and wedge 100 are both formed of suitable metallic or polymeric biomaterials. Suitable biocompatible metallic materials include pure titanium, tantalum, cobalt-chromium alloys, titanium alloys (e.g., nickel titanium alloys and tungsten titanium alloys), stainless steel alloys, molybdenum rhenium (MoRe), and NiTinol (for superelastic properties). Suitable polymeric materials include members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers. It should be appreciated that these materials may be used independently or in a composite arrangement, as desired.

Figure 5:
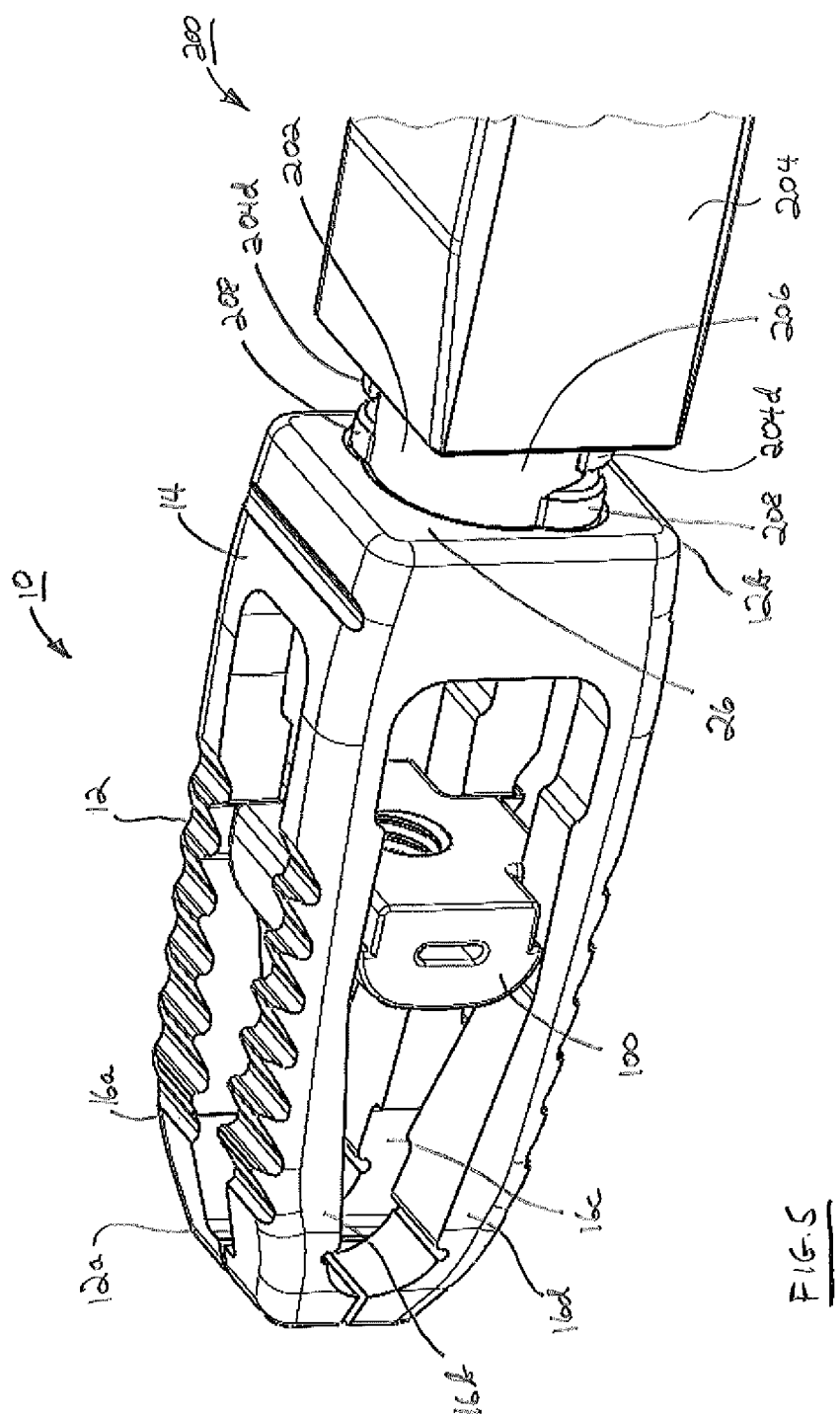
FIG. 5 is a further view of the interbody fusion device and distal end of the instrument of FIG. 2 with the distal end of the instrument moved into alignment with the interbody fusion device for attachment thereto.
Figure 12:
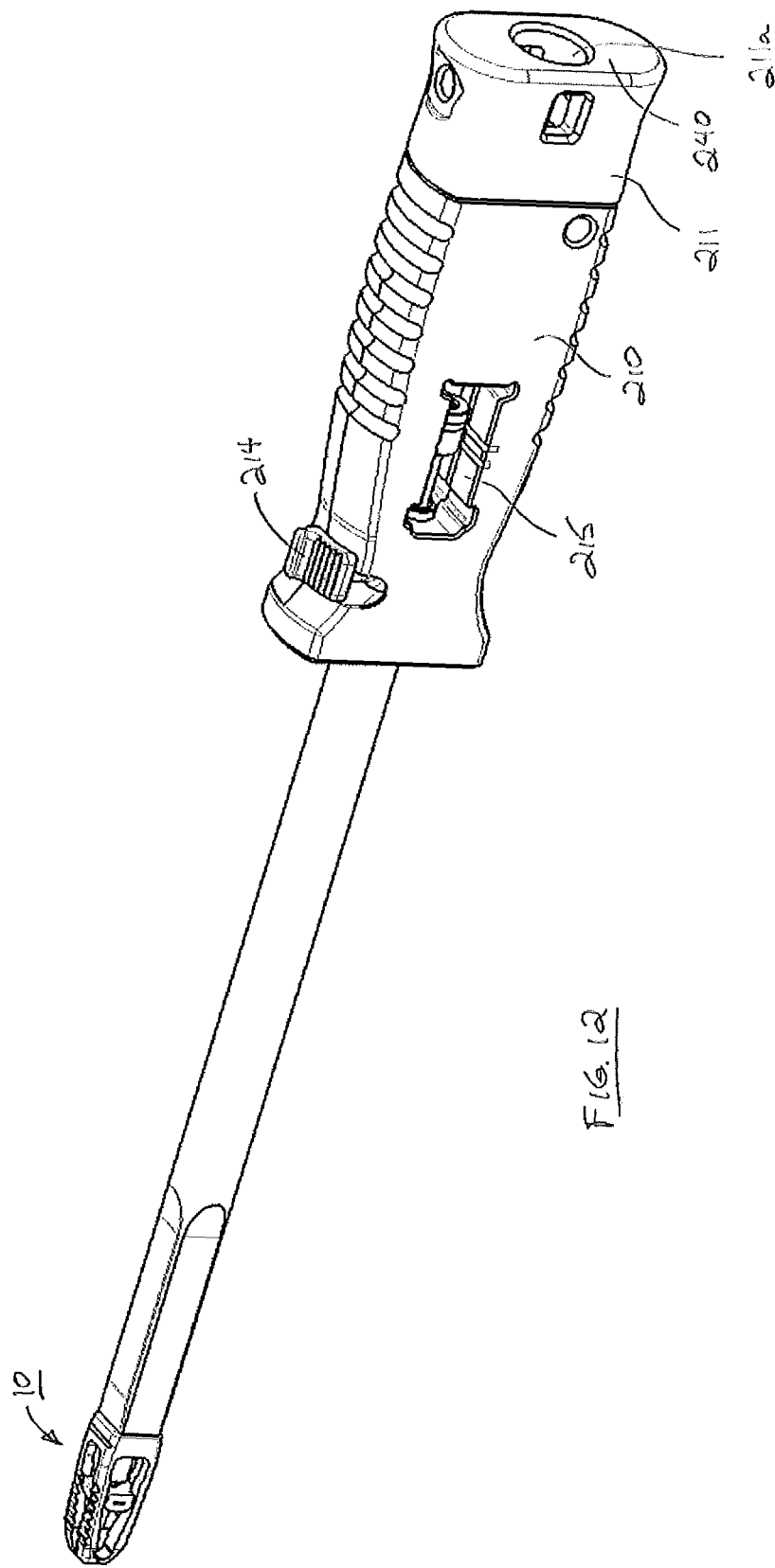
FIG. 12 is a further view of FIG. 1 showing the interbody fusion device and instrument attached with the locking handle in a vertical position upon attachment.

Referring again to FIGS. 3C, 3D, 3E and 3F, and also to FIG. 5, details of the attachment of expandable interbody fusion device 10 and instrument 200 are described. As noted above, in a particular arrangement, device 10 is sized and configured to fit into an intradiscal space through Kambin's triangle. As a result, the cross-sectional profile of device 10 as defined by its height and width is dimensioned in a manner to allow use through Kambin's triangle. In addition, since at least the distal end of the instrument 200 for inserting device 10 may also need to fit through Kambin's triangle, the dimensions of the distal end of instrument 200, including an attachment end 202, are likewise configured to be consistent with introduction through Kambin's triangle. In this manner, instrument 200 is configured to attach to proximal end 12b of cage 12 with at least the distal end of instrument 200 having a maximum dimension within the confines of the outer cross-sectional profile of cage 12.

While the size of the outer cross-sectional profile of cage 12 is configured as small as practicable for introduction through Kambin's triangle, the open interior configuration of cage 12 is desirably as large as practicable to facilitate subsequent introduction of graft material into expanded cage 12. As an example, when sized and configured for a TLIF fusion procedure at the L1/L2 lumbar level, the unexpanded height $H_1$ of cage 12 as shown in FIG. 3C may be 8.0 mm with the unexpanded width $W_1$ being 8.5 mm. As so dimensioned in this example, the outer cross-sectional profile is nearly square. To maximize graft entry into cage 12, an inner graft circular opening 24 may be provided to have a diameter of up to about 5.0 mm. As so dimensioned, the ratio of the graft opening area to the cross-sectional area of cage 12 is at least a minimum of approximately 29%. While these dimensions and minimum graft opening ratio are desirable for graft delivery, such dimensions leave relatively little material for attachment of cage 12 to instrument 200 in either the height or width directions. Accordingly, opposite diagonal corners 12d as seen in FIG. 3C are used for purposes of attachment of cage 12 to instrument 200.

FIG. 5 illustrates attachment portion 202 of instrument 200 oriented in a position ready for secured attachment to cage 12. Instrument 200, which will be described in further detail below, includes an outer tube 204 that supports a rotatable cylindrical inner tube 206. In a particular arrangement, outer tube 204 may have a rectangular cross-section not greater in size than the cross-section of the unexpanded cage 12. Inner tube 206 includes attachment portion 202 at its distal end. Attachment portion 202 comprises a pair of lugs 208 that project radially outwardly from inner tube 206 in diametrically opposite directions. As illustrated also in FIG. 3D, cage 12 comprises an instrument attachment feature 13 at base 14 that includes an outer wall 26 at proximal end 12b and an inner wall 28 spaced interiorly of outer wall 26. Inner wall 28 includes graft opening 24 in communication with cage hollow interior 12f. Outer wall 26 includes an entrance opening 30 that is in communication with graft opening 24 and cage hollow interior 12f. Entrance opening 30 has a configuration different from the configuration of graft opening 24 and in a particular arrangement has a circular portion 30a and a pair of arcuate lobes 30b that project radially outwardly from circular portion 30a in diametrically opposite directions. Lobes 30b are arranged to be disposed along a diagonal axis 12e that extends toward opposite corners 12d of cage 12 as illustrated in FIG. 3C. Axis 12e in this arrangement lies at an acute angle with respect to both the height and width of cage 12. Circular portion 30a of entrance opening 30 is sized to relatively closely receive cylindrical inner tube 206 of instrument 200, while lobes 30b are sized to relatively closely receive respective lugs 208 on inner cylindrical inner tube 206. While attachment portion 202 of instrument 200 can be received through entrance opening 30, graft opening 24 is sized to be of lesser dimension than circular portion 30a of entrance opening 30, and as such, attachment portion 202 of instrument 200 cannot pass through graft opening 24 of inner wall 28.

While entrance opening 30 is formed in one arrangement to have a circular portion with oppositely projecting lobes, it should be appreciated that other shapes of entrance opening 30 may also be provided. For example, entrance opening 30 may be formed in the shape of an oval or other shapes having a longer extent along diagonal axis 12e and a shorter extent transverse thereto.

The space between outer wall 26 and inner wall 28 defines a locking pocket 32 as depicted in FIGS. 3D and 3F. Locking pocket 32 has a circular portion 32a that is configured to receive cylindrical inner tube 206 of instrument 200 and a pair of extended lobes 32b that extend radially outwardly from circular portion 32a. Extended lobes 32b are configured to have a greater arcuate extent along the circumference of circular portion 32a than lobes 30b of entrance opening 30. As such, extended lobes 32b communicate in alignment with lobes 30b for an arcuate portion and extend arcuately further not in alignment with lobes 330b behind outer wall 26. Accordingly, once extended through entrance opening 30 as shown in FIG. 6A inner tube 206 may be rotated at a suitable angle, such that lugs 208 are arcuately moved within extended lobes 32b until lugs 208 reside between inner wall 28 and outer wall 26, as shown in FIG. 6B. In the particular example of the cage 12 having an unexpanded height $H_1$ of 8.0 mm and a width $W_1$ of 8.5 mm, inner tube 206 may be rotated approximately 41° to move lugs 208 in position between inner wall 28 and outer wall 28. Points 32c at the transition of circular portion 32a and extended lobes 32b as shown in FIG. 3F may serve as mechanical stops upon engagement by lugs 208 to prevent further rotation of attachment portion 202 within locking pocket 32. In this position attachment portion 202 may not be withdrawn from cage 12 and can be securely locked to cage 12, as will be described.

Turning now to FIGS. 7 and 8 further details of instrument 200 are described. Instrument 200 includes an elongate instrument handle 210, outer tube 204, inner tube 206 and wedge driver 212. As described, outer tube 204 may have at its distal end 204a a rectangular cross-section not greater in size than the cross-section of the unexpanded cage 12. The remaining extent of outer tube 204 may have a cylindrical outer surface 204c. Outer tube 204 has an interior lumen 204b extending longitudinally therethrough. Inner tube 206 includes attachment portion 202 at distal end 206a that comprises the pair of lugs 208 as described above. Inner tube 206 has a cylindrical exterior surface 206d for sliding engagement within lumen 204b of outer tube 204. Inner tube 206 has an interior lumen 206b extending longitudinally therethrough. A locking handle 214 is included at the proximal end 206c of inner tube 206. Locking handle 214 is fixedly secured to inner tube 206 for rotational and axial movement therewith and includes a radially projecting shaft 214a terminating in a locking lever 214b that facilitates manual rotation of locking handle 214 and hence inner tube 206, as will be described.

Wedge driver 212 comprises an elongate cylindrical shaft 212a having a distal end 212b and a proximal end 212c. Cylindrical shaft 212a is sized and configured to extend slidingly into lumen 206b of inner tube 206. A threaded portion 212d is included at the distal end 212b of shaft 212a, threaded portion 212d being configured to threadably engage threaded hole 101 of wedge 100, as will be described. An enlarged cylindrical portion 212e is disposed at the proximal end 212c of wedge driver 212.

Referring particularly now also to FIG. 8, handle 210 comprises a handle body 210a, a handle cover 210b, and an end cap 211. Handle cover 210b is suitably attached to handle body 210a by fastening members, such as set of four screws 216. End cap 211 is suitably attached to handle body 210a and may be oriented by a key 213 formed at the proximal end of handle body 210a. Handle 210 fixedly supports outer tube 204 at its distal end and includes a channel 210c adjacent its distal end for receipt and support of inner tube 206. An opening 211a extends through end cap 211 in alignment with an opening 210d through the proximal end of handle body 210a for receipt of a portion of a T-handle to drive wedge driver 212 axially distally, as will be described. A camming element 218 is supported in a pocket 220 defined by ledges 222 and 224 at the distal end of handle body 210a. Camming element 218 has an angled cam surface 218a facing proximally for interaction with cam surface 214c of locking handle 214 (See FIGS. 9B and 10B) as will be described. Camming element 218 may be secured within pocket 220 by suitable fastening members, such as screws 226 and 228. Handle body 210a supports a depressible locking button 230 adjacent the distal end of handle body 210a for pivotal movement within handle body 210a. Locking button 230 may be spring biased by a compression spring 232 captured in a recess 210e that normally biases locking button 230 in the locking position, as will be described. Handle body 210a also includes adjacent camming element 218 an opening 234 configured and sized to receive shaft 214a of locking handle 214 therein for limited rotational movement relative to handle body 210a. Handle body 210a further supports a drive nut 236. Drive nut 236 may have a substantially rectangular configuration for receipt and retention in a compatible rectangular recess 238 formed interiorly of handle body 210a. With handle cover 210b attached to handle body 210a drive nut 236 is suitably retained within handle 210 and is prevented from either axial or rotational movement therein. Drive nut 236 in a particular arrangement includes interior threads 236a for engagement with a suitable tool to drive wedge driver 212 and hence wedge 100 axially distally to expand cage 12, as will be described. A relatively flat surface 240 may be formed at the proximal end of handle end cap 211 to allow slight impaction for assisting the insertion of interbody fusion device 10 into the disc space.

Referring still to FIGS. 7 and 8, in a particular aspect, handle 210 of instrument 200 may be formed to receive a grafting cartridge to facilitate the introduction of graft material into an expanded device 10, as will be further described. In this regard, handle body 210a and handle cover 210b are formed to have side openings 215 and 217, respectively for lateral receipt of a cartridge that contains graft material. A movably releasable detent 242 that may be manually overcome upon lateral force to the cartridge may be supported in a recess 244 within handle body 210a.

Turning now to FIGS. 9A-9C, 10A-10B and 11, further details and function of the locking button 230 are described. FIGS. 9A-9C show the locking button 230 in a normally locked position. Locking button 230 is rotatably supported within handle 210 by a pivot pin 246. Locking button 230 includes a depressible portion 230a at one end and a projecting lock 230b at the opposite end. Depressible portion 230 may be of circular configuration or other suitable shape and is accessible to the user through opening 248 in handle 210. In the position shown in FIGS. 9A, 9B and 9C, biasing spring 232 urges depressible portion 230a downwardly and thereby urges lock 230b upwardly causing a free end 230c of lock 230b to enter a locking groove 214d in locking handle 214. FIGS. 10A and 10B show the locking button 230 in a released position. The user may manually push depressible portion 230a upwardly causing lock 230b at the opposite end to move downwardly, thereby moving free end 230c of lock 230b out from locking groove 214d of locking handle 214. In this position locking handle 214 may freely rotate within handle opening 234 as shown in FIG. 11, thereby causing rotation of inner shaft 206 relative to handle 210. In this position, free end 230d of lock 230b may reside in a secondary groove 214e in locking handle 214 that may be overcome upon rotating locking handle 214 back to the locked position. The position of locking handle 214 in FIG. 11 is the same as the locking handle 214 as shown in FIG. 1.

Having described the details of interbody fusion device 10 and instrument 200, use of instrument 200 to insert device 10 into a disc space between two opposing vertebral bodies, expand device 10 therein and facilitate graft delivery into expanded device 10 is now described. An incision is made through tissue of a patient to establish a working corridor to the spinal surgical site, for example, through Kambin;s triangle, for a TLIF procedure. The corridor may be formed with suitable instruments and the disc space may be suitably prepared through the corridor for insertion of interbody fusion device 10. Instrument 200, without wedge driver 212, may be attached to device 10 by initially aligning lugs 208 at attachment end 202 of inner tube 206 with lobes 30b of opening 30 at outer wall 26 of cage 12, as depicted in FIG. 2. Attachment end 202 may then be inserted into cage 12 through opening 30 as illustrated in FIG. 5 and into locking pocket 32 with lugs 208 being situated within extended lobes 32b, as shown in FIG. 6A. At this point, locking handle 214 is in an angular position relative to handle 210 as shown in FIG. 1. Locking handle 214 is then rotated manually in a clockwise direction looking from the proximal end of instrument 200 toward the patient until handle 214 is in the vertical position as shown in FIGS. 9A-9C and 12. Structural features, such as projections 204d (see FIGS. 2 and 5) at the distal end of outer tube 204 enter and engage the lobes 30b at the proximal end of device 10 to prevent relative rotation between outer tube 204 and device 10 during rotation of locking handle 214. In the above example of a cage 12 having an unexpanded height $H_1$ of 8.0 mm and a width $W_1$ of 8.5 mm, locking handle 214 may be rotated approximately 41°. During rotation of locking handle 214 to the vertical position, shaft 214a of locking handle 214 engages locking button 230 and pushes locking button 230 axially proximally against the bias of spring 232. As locking handle 214 reaches the vertical position shown in FIG. 12 free end 230c is moved out from secondary grove 214e of locking handle 214 allowing locking button 230 to snap free end 230c of lock 230b into locking grove 214d to thereby lock locking handle 214 in such position until locking button 230 is manually depressed upwardly relative to handle 210.

During such rotation of locking handle 214 lugs 208 are moved arcuately to extend into extended lobes 32b behind outer wall 26, as illustrated in FIG. 6B. In this position, proximal wall 26 is captured between lobes 208 and the distal end 204a of outer tube 204 of instrument 200. Simultaneously during such rotation cam surface 214c on locking handle 214 slidingly engages cam surface 218a on camming element 218 causing inner tube 206, which is securely affixed to locking handle 214, to move slightly axially proximally relative to handle 210. The amount of axial proximal movement of inner tube 206 is sufficient to cause outer wall 26 to be sandwiched between lobes 208 at the distal end of inner tube 206 and the distal end 204a of outer tube 204. Upon locking handle 214 reaching the vertical position shown in FIG. 12 sufficient compression force is applied to outer wall 26 to securely tighten instrument 200 to cage 12 of device 10.

Upon attachment of instrument 200 to cage 12 instrument 200 is used to insert device 10 into the suitably prepared disc space. Flat surface 240 of instrument handle 210 may be appropriately tapped or malleted to gently urge device 10 into the disc space, if desired by the surgeon. Wedge driver 212 is then introduced into lumen 206b of inner tube 206 and threaded portion 212d is manually threaded into threaded hole 101 of wedge 100 to suitably attach wedge 100 to wedge driver 212. Wedge driver 212 may alternatively in accordance with the surgeon's practice be attached to wedge 100 prior to introduction of device 10 into the disc space. Once attached, wedge driver 212 may be suitably driven axially distally to push wedge 100 axially distally within cage 12 to expand cage 12 within the disc space as described above. Wedge 100 which is initially disposed approximately centrally between distal end 12a and proximal end 12b of cage 12 is moved toward distal end 12a until engagement edges 106a, 106b, 106c and 106d engage and reside in respective locking notches 23a, 23b, 23c and 23d to lock cage 12 in the expanded position as shown in FIG. 13A A suitable tool to drive wedge driver 212 and hence wedge 100 axially may be a T-handle (not shown). Such a T-handle may have an elongate cylindrical tube that has external threads at a distal end. T-handle may be configured such that the cylindrical tube slides within opening 211a of handle end cap 211 until the external threads at the distal end of the T-handle are threadably received within interior threads 236a of drive nut 236. An interior transverse surface may be provided within T-handle to engage enlarged cylindrical portion 212e at the proximal end 212c of wedge driver 212. Suitable rotation of T-handle will cause T-handle to move axially distally relative to handle 210 under the influence of the threaded engagement between external threads of the T-handle and interior threads 236a of drive nut 236, causing interior transverse surface of T-handle to push against enlarged cylindrical portion 212e and thereby push wedge driver 212 axially in the distal direction. Such rotation of T-handle is continued until cage 12 is properly expanded as shown in FIGS. 13A-13C and wedge 100 is suitably locked within locking notches 23a-d.

Figure 14:
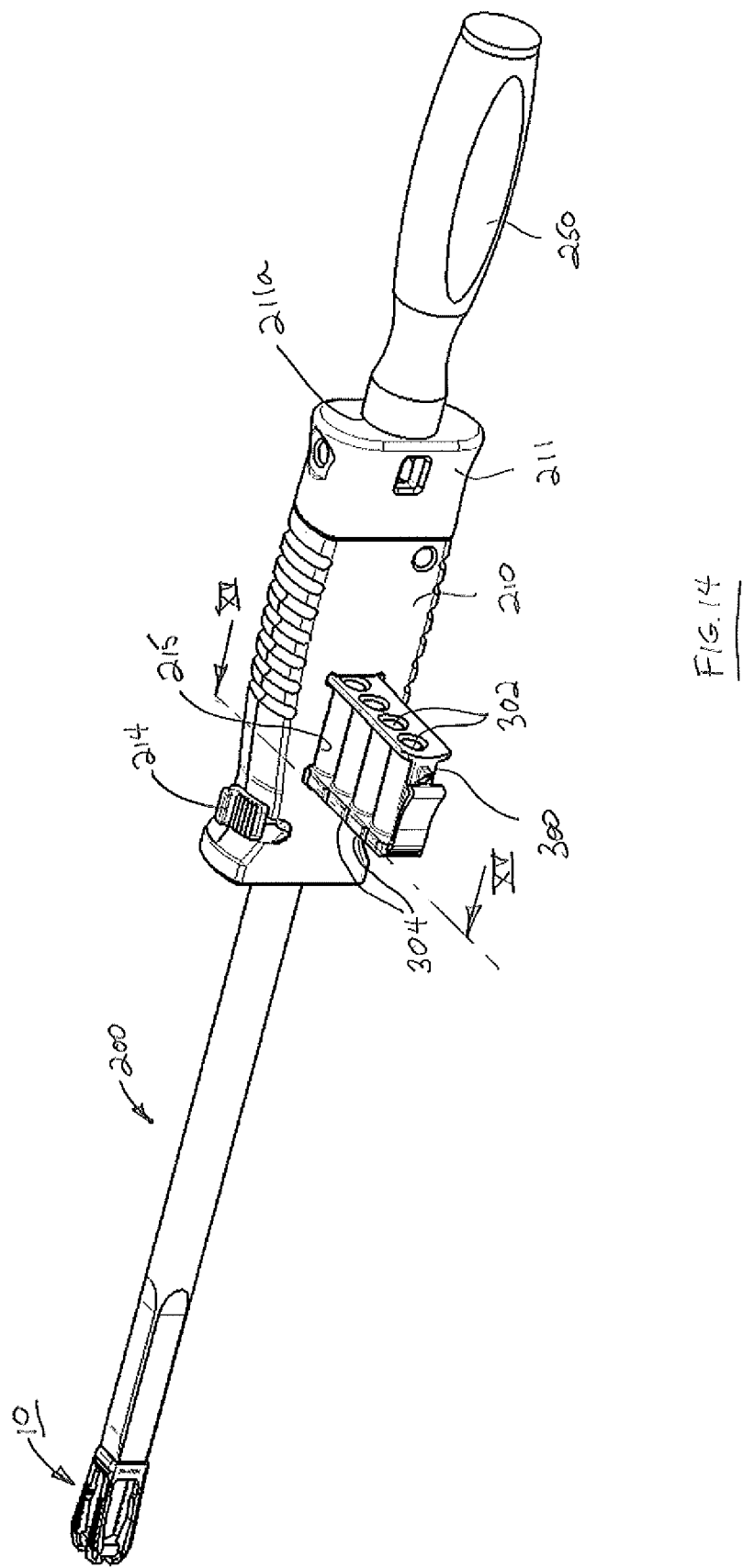
FIG. 14 is a further view of FIG. 12 showing a graft delivery cartridge holding a plurality of graft pellets positioned laterally in the instrument for individual delivery of graft pellets to the expanded interbody fusion device.
Figure 15:
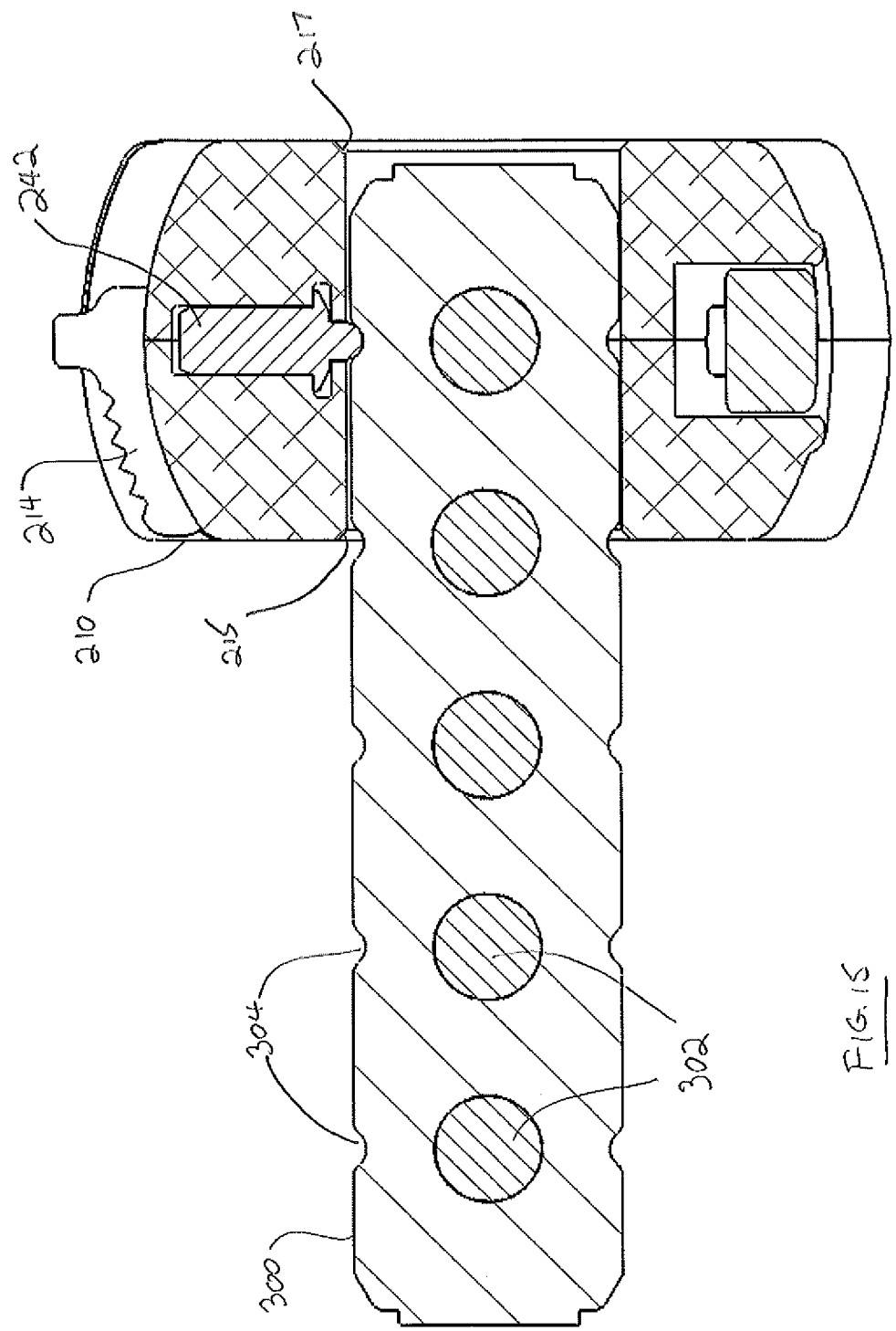
FIG. 15 is a cross-sectional view of the instrument of FIG. 14 as seen along viewing lines XV-XV.

After interbody fusion device 10 is expanded, wedge driver 212 and, if used, the T-handle, may be removed from instrument 200, which remains attached to expanded device 10. Graft material may be introduced into expanded interbody fusion device 10 using instrument 200. As shown in FIGS. 14 and 15, an elongate cartridge 300 containing a plurality of individually spaced pellets 302 of graft material may be slidingly inserted into opening 215 in the side of instrument handle 210 as illustrated in FIG. 14. Cartridge 300 may contain any suitable number of individual pellets 302, with five pellets being shown in FIG. 15. Cartridge 300 includes a plurality of recesses 304, each of which is associated and aligned with one of the individual pellets 302. Each recess 304 is configured to receive movably releasable detent 242 as depicted in FIG. 15. Receipt of detent 242 into a respective recess 304 tentatively holds cartridge 300 in a position such that one of the pellets is aligned with interior lumens 206b and 204b of inner tube 206 and outer tube 204, respectively. As a manual force is applied against cartridge 300 in the lateral direction, the tentative position is overcome as detent 242 is moved transversely out from a respective recess 304 allowing cartridge 300 to move further into handle 210 until another recess 304 is aligned with detent 242. Cartridge 300 may be moved laterally through handle 210 until it emerges through opening 217 on the opposite side of handle 210, at which time it may be removed. As each pellet 302 is aligned with inner tube 206 and outer tube 204, a suitable plunger 250 may be introduced through opening 211a of handle end cap 211 to push pellets 302 individually one at a time through graft opening 24 into interior hollow 12f of expanded interbody device 10 until sufficient graft material has been placed. As noted above, graft opening 24 of cage 12 of interbody fusion device 10 may in some instances be provided to have a diameter of up to about 5.0 mm, which facilitates an effective and easy delivery of a suitable quantity of graft material. As graft material fills interior hollow 12f graft material may further pass through cage top opening 11 and bottom opening 13 to make contact with the endplates of opposing vertebral bodies of a spine to facilitate fusion thereto. Graft material may also emanate from cage side openings 15 and 17 so as to occupy the intervertebral space adjacent cage 12 to promote additional fusion to the opposing vertebral bodies.

As an alternative, a separate graft delivery device may be used in conjunction with instrument 200 to deliver an appropriate amount of graft material to the surgical site and into expanded device 10. One such suitable graft delivery device is described in U.S. Pat. No. 10,492,925, issued on Dec. 3, 2019 to Hollister et al. (the '925 Patent) and assigned to the same assignee as the subject application. The entire contents of the '925 Patent are incorporated herein by reference. The graft delivery device described in the '925 Patent is commercially available under the brand name GraftMag. In use, the channel 12 described in the '925 Patent made be introduced through inner tube 206 of instrument 200 to place graft into device 10 through opening 30 of cage 12.

Upon delivery of suitable graft material and completion of the surgical procedure, instrument 200 may then be detached from the expanded cage 12. To effect such detachment depressible portion 230a of locking button 230 is manually depressed upwardly releasing lock 230b from locking groove 214d as described hereinabove thereby allowing locking handle 214 to move radially within opening 234 of handle 210 to the angular position shown in FIG. 1. During such movement, the compression of cage outer wall 26 between lugs 208 and the distal end 204a of instrument outer tube 204 is loosened while lugs 208 are radially moved back into alignment with lobes 30b. At this point, instrument 200 may be withdrawn from expanded device 10 and from the surgical site.

In the example provided above for use in a TLIF fusion procedure at the L1/L2 lumbar level, cage 12 may have an unexpanded height $H_1$ of 8.0 mm and an unexpanded width $W_1$ of 8.5 mm. Upon expansion, distal end 12a of cage may be increased to an expanded height $H_2$ of 10 mm and an expanded width $W_2$ of 11 mm, as shown in FIGS. 13A, 13B and 13C. The increase in height to $H_2$ results in a lordotic angle of eight degrees at distal end 12a and an increase in the width of cage 12 at distal end 12a of approximately 29%. As noted above, interbody fusion device 10 may also be used in TLIF fusion procedures at other spinal levels. For example, cage 12 when used in a TLIF fusion procedure at the L4/L5 level may have an unexpanded height $H_1$ of 16.0 mm and an unexpanded width $W_1$ of 8.5 mm consistent with introduction through Kambin's triangle. Upon expansion, distal end 12a of cage 12 at this level may be increased to an expanded height $H_2$ of 18 mm resulting in a lordotic angle of eight degrees and an expanded width $W_2$ of 11 mm. At such other level, cage 12 may have an opening 30 at the proximal end 12b of 5.0 mm to be compatible with the graft delivery instruments, although other suitable dimensions for opening 30 may be used.

Figure 16:
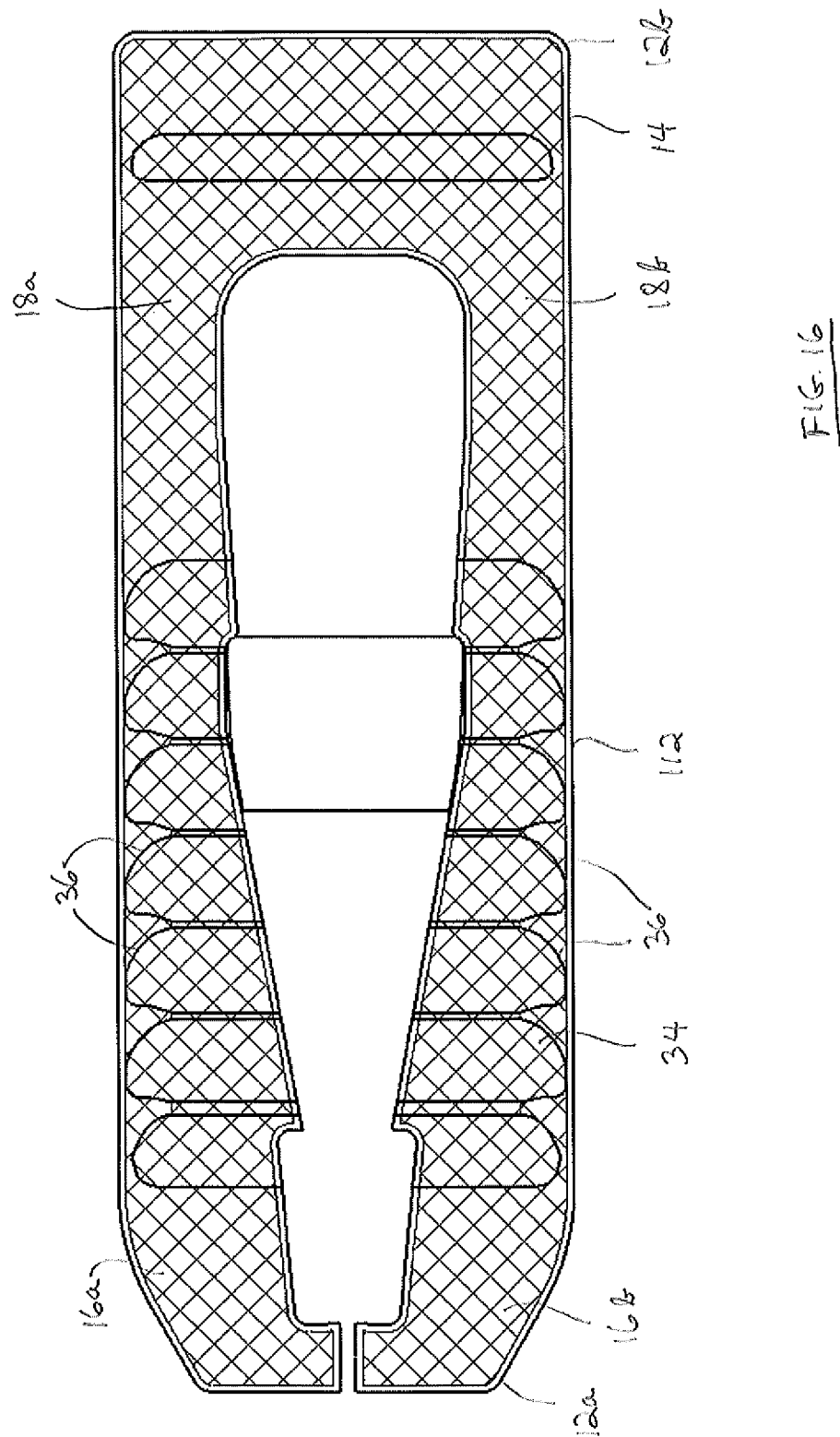
FIG. 16 is a top plan view of an unexpanded interbody fusion device having surface texturing in accordance with a particular aspect of the device.

Turning now to FIG. 16, a cage 112 that is a variation of cage 12 is shown. Cage 112 is identical to cage 12 except for the provision of textured top and bottom surfaces. Since the texturing of both top and bottom surfaces are the same, only the details of top textured surface are shown and described, it being understood that the details of bottom textured surface are the same. Textured top surface 34 is formed on both upper arms 16a and 16b. As shown, textured top surface 34 is formed on the entire top surface 34 of upper arms 16a and 16b. In some instances, texturing may be included only on those portions that are configured to contact a vertebral endplate of a superior vertebral body adjacent the disc space. The textured surface includes those upper portions of arms 16a and 16b that have fixation structures, such as a plurality of serrations 36. Such serrations 36 are not included adjacent hinge points 18a and 18b. In other instances, no textured surfaces may be formed at the distal end 12a of cage 112 that is curved in a manner to facilitate entrance of cage 112 into the disc space.

Textured surface 34 may be formed in a three-dimensional geometric pattern having a plurality of projections and recesses. Such a pattern may be formed by various methods, including without limitation, laser ablation, acid etching and machining. Textured surfaces in such a pattern are believed to promote the formation of intimate tissue integration between the endplates of the opposing vertebral bodies and cage 112. In a particular arrangement where cage 112 is formed of titanium, textured surface 34 may be formed by ablating the upper and lower surfaces of cage 112 by a pulsed laser in the nanosecond range to create a porous surface comprising projections and recesses having a depth of up to at least 100 μm. Such a process may be performed in accordance with the nanosecond laser devices and methods taught and described, for example, in U.S. Pat. No. 5,473,138, entitled "Method for Increasing the Surface Area of Ceramics, Metals and Composites", issued to Singh et al on Dec. 5, 1995, the entire contents of which are incorporated herein by reference.

In an effort to further enhance the tissue integration aspects of cage 112, textured upper surface 34 may be subsequently treated by further ablating those previously formed surfaces by an ultrafast pulsed laser to create additional, smaller projections and recesses having a depth less than 1 μm and preferably not greater than 200 nm. Such a process may be performed with a picosecond pulsed laser or a femtosecond pulsed laser device in accordance with, for example, the methods and laser devices taught and described in U.S. Pat. No. 6,951,627, entitled "Method of Drilling Holes With Precision Laser Micromachining", issued October 2005 to Li et al., the entire contents of which are incorporated by reference herein. Other picosecond and femtosecond pulsed lasers may also be used, such as those described in U.S. Pat. No. 10,603,093, entitled "Bone Implant and Manufacturing Method Thereof", issued on Mar. 31, 2020 to Lin et al., the contents of which are incorporated by reference in their entirety. In a particularly preferred arrangement, textured surface 34 is formed by initially laser ablating the surfaces of cage 112 with the nanosecond laser devices to form a porous surface followed by laser ablation with the femtosecond laser to further alter the surface to produce nano-scale structures.

While the invention has been illustrated and described in detail in the drawings and foregoing description, the same should be considered as illustrative and not restrictive in character. For example, the inventive concepts described herein may be used with non-expandable as well as expandable spinal implants, and the textured surfaces formed by the laser ablation processes described herein may also be used with other spinal implants and in spinal surgical procedures other than TLIF applications. Accordingly, it is understood that only the preferred embodiments have been presented and that all changes, modifications and further applications that come within the spirit of the invention are desired to be protected.

What is claimed is:

1. A process of forming textured surfaces on an interbody fusion device that comprises a cage having a top surface and an opposite bottom surface, said textured surfaces being prepared by a process comprising the steps of:
   initially laser ablating said top surface and said bottom surface of said cage with a nano- second pulsed laser to form a three-dimensional geometric pattern on each of said top surface and said bottom surface that comprises projections and recesses; and
   then, laser ablating said initially ablated top surface and said bottom surface of said cage with an ultrafast pulsed laser to form nano-scale structures on said top surface and bottom surface, said nano-scale structures having a depth less than 1 μm.

2. An interbody fusion device comprising a cage with textured top and bottom surfaces prepared by the process of claim 1.

3. The process of claim 1, wherein said laser ablation of said initially ablated top and bottom surfaces with an ultrafast pulsed laser is conducted with a femtosecond pulsed laser such that said nano-scale structures have a depth not greater than 200 nm.

4. An interbody fusion device comprising a cage with textured top and bottom surfaces prepared by the process of claim 3.

5. The interbody fusion device of claim 4, wherein said cage is formed of titanium or titanium alloys.

6. A process of forming textured surfaces on an interbody fusion device that comprises a cage having a top surface and an opposite bottom surface, said textured surfaces being prepared by a process comprising the steps of:
   initially forming a three-dimensional geometric pattern on each of said top surface and said bottom surface by laser ablating said respective top and bottom surfaces with a nano-second laser to form projections and recesses having a depth of up to at least 100 μm; and
   then, laser ablating said three-dimensional geometric pattern surface on each of said top surface and said bottom surface of said cage with an ultrafast pulsed laser to form nano-scale structures on projections and within said recesses that have a depth less than 1 μm.

7. The process of claim 6, wherein said nano-scale structures on each of said top surface and said bottom surface are formed with a picosecond pulsed laser.

8. The process of claim 6, wherein said nano-scale structures on each of said top surface and said bottom surface are formed with a femtosecond pulsed laser.

9. The process of claim 8, wherein said nano-scale structures on each of said top surface and said bottom surface are formed to have projections and recesses having a depth not greater than 200 nm.

10. An interbody fusion device comprising a cage with textured top and bottom surfaces prepared by the process of claim 9.

11. The interbody fusion device of claim 10, wherein said cage is formed of titanium or titanium alloys.

12. An interbody fusion device comprising a cage with textured top and bottom surfaces prepared by the process of claim 6.

13. A process of forming textured surfaces on an interbody fusion device that comprises a cage having a top surface and an opposite bottom surface, said textured surfaces being prepared by a process comprising the steps of:
   initially forming a three-dimensional geometric pattern on each of said top surface and said bottom surface by ablating each of said top surface and said bottom surface with a nanosecond laser to form a plurality of projections and recesses; and
   then, further laser ablating said initially laser ablated top surface and bottom surface of said cage with a femtosecond pulsed laser to form nano-scale structures on said projections and within said recesses of said top surface and bottom surface.

14. The process of claim 13, wherein said projections and recesses have a depth of up to at least 100 μm.

15. The process of claim 14, wherein said nano-scale structures on said projections and within said recesses on said top surface and said bottom surface are formed to have a depth not greater than 200 nm.

16. An interbody fusion device comprising a cage with textured top and bottom surfaces prepared by the process of claim 15.

17. An interbody fusion device of claim 16, wherein said cage is formed of titanium or a titanium alloy.

* * * * *